(12) United States Patent
Maguire

(10) Patent No.: US 9,545,370 B2
(45) Date of Patent: *Jan. 17, 2017

(54) BIOACTIVE COMPOSITIONS AND METHODS FOR THEIR PREPARATION AND USE

(71) Applicant: BioRegenerative Sciences, Inc., San Diego, CA (US)

(72) Inventor: Greg Maguire, San Diego, CA (US)

(73) Assignee: BIOREGENERATIVE SCIENCES, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/539,910

(22) Filed: Nov. 12, 2014

(65) Prior Publication Data

US 2015/0071877 A1 Mar. 12, 2015

Related U.S. Application Data

(63) Continuation-in-part of application No. 14/218,926, filed on Mar. 18, 2014, which is a continuation of application No. 13/466,132, filed on May 8, 2012, now abandoned.

(51) Int. Cl.
| | | |
|---|---|---|
| A61K 35/33 | (2015.01) | |
| A61K 35/28 | (2015.01) | |
| A61K 8/64 | (2006.01) | |
| C12N 5/0775 | (2010.01) | |
| A61K 8/65 | (2006.01) | |
| A61Q 7/00 | (2006.01) | |
| A61K 31/728 | (2006.01) | |
| A61K 35/12 | (2015.01) | |

(52) U.S. Cl.
CPC . *A61K 8/65* (2013.01); *A61K 8/64* (2013.01); *A61K 31/728* (2013.01); *A61K 35/12* (2013.01); *A61K 35/28* (2013.01); *A61K 35/33* (2013.01); *A61Q 7/00* (2013.01); *C12N 5/0667* (2013.01); *A61K 2800/59* (2013.01); *C12N 2502/09* (2013.01); *C12N 2502/092* (2013.01); *C12N 2502/1323* (2013.01); *C12N 2502/1382* (2013.01)

(58) Field of Classification Search
CPC .......... A61K 35/33; A61K 35/28; A61K 8/64; A61K 2800/59; C12N 5/0667; C12N 2502/1382

See application file for complete search history.

(56) References Cited

U.S. PATENT DOCUMENTS

| | | | |
|---|---|---|---|
| 5,091,173 A | 2/1992 | Buultjens et al. | |
| 5,709,854 A | 1/1998 | Griffith-Cima et al. | |
| 6,372,494 B1 | 4/2002 | Naughton et al. | |
| 6,692,738 B2 | 2/2004 | MacLaughlin et al. | |
| 7,449,333 B2 | 11/2008 | Rolland et al. | |
| 7,459,307 B2 | 12/2008 | Ha et al. | |
| 8,535,913 B2 | 9/2013 | Naughton et al. | |
| 2008/0274185 A1 | 11/2008 | Mao | |
| 2011/0294731 A1* | 12/2011 | Torfi ................... A61Q 19/08 514/7.6 |
| 2011/0300097 A1* | 12/2011 | Al-Qahtani .......... A61K 9/0048 424/85.2 |
| 2012/0141410 A1* | 6/2012 | Torfi .................. C07K 14/4727 424/85.2 |
| 2012/0207705 A1 | 8/2012 | Kara | |
| 2013/0302273 A1 | 11/2013 | Maguire et al. | |
| 2015/0071877 A1 | 3/2015 | Maguire et al. | |

FOREIGN PATENT DOCUMENTS

WO    WO 2011/136433 A1    11/2011

OTHER PUBLICATIONS

Amirjamshidi et al. Mol Vis. Mar. 8, 2011;17:658-666.*
Oh et al., Stem Cells. Apr. 2008;26(4):1047-1055.*
Polisetty et al., Mol Vis. Mar. 4, 2008;14:431-442.*
Amirjamshidi et al., "Limbal fibroblast conditioned media: A non-invasive treatment for limbal stem cell deficiency." Mol. Vis. Mar. 8, 2011. 17:658-66.
Brigham, Pamela A et al., (1988), "The Stumptailed macaque as a Model for Andro-genetic Alopecia: Effects of Topical Minoxidil Analyzed by Use of the Folliculogram", Clin. Dermatol., 6(4):177-187.
Diani AR et al., (1994), "Immunocytochemical Localization of Androgen Receptors in the Scalp of Stumptail Macaque Monkey, a Model of Androgenetic Alopecia", Invest. Dermatol., 102(4):511-514.
Doyle et al., *Cell & Tissue Culture: Laboratory Procedures in Biotechnology*, John Wiley & Sons Ltd., 1998, Chichester, England.
Flax et al., (1998), "Engraftable human neural stem cells respond to developmental cures, replace neurons, and express foreign genes", Nature Biotechnol., 16(11):1033-1039.
Frisen et al., (1998), "Central nervous system stem cells in the embryo and adult", Cell. Mol. Life Sci., 54:935-945.
Holland, J Michael et al., (1988), "Animal Models of Alopecia", Clin. Dermatol., 6(4):159-162.
Hussein Atif M., (1995), "Protection Against Cytosine Arabinoside-Induced Alopecia by Minoxidil in a Rat Animal Model", Int. J. Dermatil., 34(7):470-473.

(Continued)

*Primary Examiner* — Daniel C Gamett
(74) *Attorney, Agent, or Firm* — Knobbe, Martens, Olson & Bear, LLP

(57) ABSTRACT

A method for preparing a bioactive composition containing conditioned cell culture medium is disclosed. The method comprises culturing cells of two or more eukaryotic cell line to form conditioned culture media, separating the cultured cells from the conditioned culture media, and combining conditioned culture media to form a bioactive composition. Novel bioactive compositions, formulations and their use in treating of a variety of diseases and health conditions are also disclosed.

21 Claims, 2 Drawing Sheets

(56) References Cited

OTHER PUBLICATIONS

Invitrogen User Manual, *StemPro® human Adipose-Derived Stem Cells*, Catalog Nos. R7788-110 and R7788-115, A10296, Version D, Feb. 13, 2009, 36 pages.

Keller et al., (1999), "Human embryonic stem cells: The future is now", Nature Med., 5(2):151-152.

Kuno et al., (2011), "Recent Advances in Ocular Drug Delivery Systems", Polymers, 3:193-221.

Liss, Alan R., *Culture of Animal Cells: A Manual of Basic Technique*, $2^{nd}$ Edition, Edited by R. Ian Freshney, Table of Contents, 1987, New York.

Liss, Alan R., *Methods for Preparation of Media, Supplements and Substrate for Serum-Free Animal Cell Culture*, Table of Contents, New York, 1984.

MacKay et al., (1998), "Chondrogenic Differentiation of Cultured Human Mesenchymal Stem Cells from Marrow", Tissue Eng., 4:415-428.

McElwee KJ et al., (1990), "Immunobiological studies on the alopecic (DEBR) rat", Br. J. Dermatol., 123(5):557-567.

Neste DV, (1996), "The Growth of Human Hair in Nude Mice", Dermatol. Clin., 14(4):609-617.

Oh et al., "The Anti-Inflammatory and Anti-Angiogenic Role of Mesenchymal Stem Cells in Corneal Wound Healing Following Chemical Injury." Stem Cells. Apr. 26, 2008(4):1047-55.

Oliver RF et al., (1991), "The DEBR Rat Model of Alopecia Areata", J. Invest. Dermatol., 96(5):978.

Pan HJ et al., (1998), "Evaluation of RU58841 as an Anti-Androgen in Prostate PC3 Cells and a Topical Anti-Alopecia Agent in the Bald Scalp of Stumptailed Macaques", Endocrine, 9(1):39-43.

Park, Byung-Soon et al., (2010), "Hair growth stimulated by conditioned medium of adipose-derived stem cells is enhanced by hypoxia: evidence of increased growth factor secretion", Biomedical Research 31(1):27-34.

Polisetty et al., "Mesenchymal cells from limbal stroma of human eye." Mol Vis. Mar. 4, 2008. 14:431-42.

*Remington: The Science and Practice of Pharmacy*, $20^{th}$ Ed., Table of Contents, Lippincott Williams & Wilkins, Baltimore, Md, 2000.

Rittmaster RS et al., (1987), "The Effects of $N,N$-Diethyl-4-Methyl-3-Oxo-4-Aza-5α-Androstane-17β-Carboxamide, a 5α-Reductase inhibitor and Antiandrogen, on the Development of Baldness in the Stumptail Macaque*", J. Clin. Endocrinol. Metab., 65(1):188-93.

ScienCell Research Laboratories. HDF-f Catalog No. 2300, Human Dermal Fibroblasts-fetal (HDF-f), Product Sheet retrieved Apr. 15, 2016 from http://www.sciencellonline.com/site/productInformation.php?keyword=2300, 3 pages.

ScienCell Research Laboratories. HHDPC Catalog No. 2400, Human Hair Dermal Papilla Cells (HHDPC), Product Sheet retrieved Apr. 15, 2016 from http://www.sciencellonline.com/site/productInformation.php?keyword=2400, 3 pages.

Shamblott et al., (1998), "Derivation of pluripotent stem cells from cultured human primordial germ cells", PNAS, 95:13726-1371.

Smith, (1998), "Cell therapy: In search of pluripotency", Curr. Biol., 8:R802-804.

Thomson et al., (1998), "Embryonic Stem Cell Lines Derived from Human Blastocysts", Science, 282:1145-1147.

Williams et al., (1999), "Cells Isolated from Adult Human Skeletal Muscle Capable of Differentiating into Multiple Mesodermal Phenotypes", Am. Surg., 65:22-26.

Non-Final Office Action mailed May 3, 2013 for U.S. Appl. No. 13/466,132, filed May 8, 2012.

Amendment filed Aug. 5, 2013 for U.S. Appl. No. 13/466,132, filed May 8, 2012.

Final Office Action mailed Oct. 7, 2013 for U.S. Appl. No. 13/466,132, filed May 8, 2012.

Notice of Abandonment mailed Mar. 21, 2014 for U.S. Appl. No. 13/466,132, filed May 8, 2012.

Request for Express Abandonment filed Mar. 18, 2014 for U.S. Appl. No. 13/466,132, filed May 8, 2012.

Final Office Action for U.S. Appl. No. 14/218,926 dated Dec. 15, 2015.

Office Action for U.S. Appl. No. 14/218,926 dated Jun. 29, 2015.

\* cited by examiner

BIOACTIVE COMPOSITIONS AND METHODS FOR THEIR PREPARATION AND USE

CROSS-REFERENCE TO RELATED APPLICATIONS

This application is a continuation in part (CIP) of U.S. patent application Ser. No. 14/218,926, filed on Mar. 18, 2014, which is a CIP application of U.S. patent application Ser. No. 13/466,132, filed on May 8, 2012. The disclosures of the above-referenced applications are herein expressly incorporated by reference in their entireties.

FIELD

The present disclosure relates to the fields of development, cell biology, molecular biology, and genetics. More particularly, the disclosure relates to a method of making a bioactive composition comprising culture media that have been conditioned by cells of two or more animal cell lines such as, for example, stem cell lines.

BACKGROUND

Unless otherwise indicated herein, the materials described in this section are not prior art to the claims in this application and are not admitted to be prior art by inclusion in this section.

Regenerative medicine utilizing conditioned media derived from cell cultures, such as stem cell cultures, increasingly attracts attention as a versatile alternative technique for treating diseases that are difficult to treat by conventional medicine. For example, one of the major unmet needs in medicine today is a treatment for diseases and conditions that involve complex, multi-molecular processes that cannot simply be replicated by administration of a single growth factor.

Experimental data of the use of conditioned culture media in the treatment of various diseases and health conditions have been accumulating in recent years. Several studies reported beneficial effects of stem cell therapy in degenerative diseases such as myocardial infarction and revealed that stem cells cause tissue repair due to their ability to secrete trophic factors that exert beneficial impact on the damaged tissue, rather than their capacity to differentiate into the needed cells. Various studies on stem cell-derived secreted factors have showed that the secreted factors alone without the stem cell itself may cause tissue repair in various conditions that involved tissue/organ damage. Further, it has been reported that stem cells provide the extracellular microenvironment with a wide range of growth factors, cytokines and chemokines, which are often broadly defined as the stem cells secretome and can include micro-vesicles or exosomes. In in vitro condition, these molecules can be traced from the conditioned medium or spent media harvested from cultured cells, and thus the medium comprising these secreted cellular factors is called conditioned culture medium. Conditioned medium now serves as a new treatment modality in regenerative medicine and has shown a successful outcome in some diseases.

As technologies advance and stem cell lines and other requisites become available, there is a continued need to develop formulations for treatment of tissue related diseases and associated symptoms. The use of secretome-containing conditioned culture media have several advantages compared to the use of stem cells, as conditioned culture media can be manufactured, freeze-dried, packaged, and transported more easily. Moreover, as described in some particular alternatives of the present disclosure, as conditioned culture media are devoid of cells; there is no need to match the donor and the recipient to avoid rejection problems. Therefore, conditioned culture media have a promising prospect to be produced as pharmaceuticals for regenerative medicine.

SUMMARY

The present disclosure generally relates to bioactive compositions and formulations comprising conditioned culture media, and methods for making or using same. Some aspects and alternatives disclosed herein relate to a method for making a bioactive composition. Certain aspects and alternatives disclosed herein relate to a bioactive formulation. Further aspects and alternatives disclosed herein relate to a method for treating an eye condition in a subject in need thereof. Further aspects and alternatives disclosed herein relate to a method treating a hair condition in a subject by stimulating hair growth in the subject.

In one aspect, some alternatives disclosed herein relate to a method for making a bioactive composition. The method includes culturing cells of a first cell line and a second cell line in a first and a second culture medium, wherein the cells secrete extracellular products into the respective culture medium so that a first conditioned culture medium and a second conditioned culture medium are respectively formed; optionally culturing cells of a third cell line in a third culture medium wherein the cells secrete extracellular products into the culture medium so that a third conditioned culture medium is formed; separating the first, second, and optionally third conditioned culture media from the respective cultured cells; and combining the first and the second conditioned culture media, and optionally the third conditioned culture medium, to form a bioactive composition. In the method, the first, second, and optionally third cell lines are different from one another and are each selected from the group consisting of an adipose-derived stem cell (ADSC) line, a non-adipose mesenchymal stem cell line, a fibroblast cell line, a hair dermal papilla (HDP) cell line, and a limbal stem cell line.

Implementations of the method according to this aspect of the disclosure can include one or more of the following features. The first cell line, in some particular alternatives, is an ADSC line. In some alternatives, the second cell line is a fibroblast cell line. In some alternatives, the bioactive composition includes culture medium conditioned by cells of a third cell line. In some particular alternatives, the third cell line is a limbal cell line. In some other particular alternatives, the third cell line is an HDP cell line. In yet some other alternatives, at least one of the cell lines is human cell line.

In some particular alternatives of this aspect and other aspects of the disclosure, each of the culturing steps is performed for at least 2 days, at least 5 days, at least 7 days, at least 8 days, or at least 10 days. In some alternatives, each of the culturing steps is carried out until said culture reaches at least 85%, at least 90%, at least 95%, or at least 98% cell confluence. In some particular alternatives, the cells of at least one of the cell lines have been passaged multiple times to produce the conditioned culture media. In some particular alternatives, the cells of at least one of the cell lines have been passaged at least 2, 3, 4, 5, 6, 7, 8, 9, or 10 times to produce said conditioned culture media. In certain alternatives, the cells of at least one of the cell lines are passaged after reaching at least 85%, at least 90%, at least 95%, or at least 98% cell confluence. In some other alternatives, the bioactive composition includes a ratio of the first conditioned culture medium to the second conditioned culture medium of between about 1:10 to about 10:1. In some particular alternatives, the ratio of the first conditioned culture medium to the second conditioned culture medium is about 1:1.

In some alternatives, the method for making a bioactive composition disclosed herein further includes formulating the bioactive composition to form an aerosol, a cream, a dispersion, an emulsion, a film, a foam, a gel, a liquid, a lotion, a lyophilisate, a mousse, an ointment, a powder, a solid, a spray, or a suspension. In some alternatives, the bioactive composition is suitable for a cosmetic application, a medicinal application, a neutraceutical application, or a pharmaceutical application.

In one aspect, the present disclosure further relates to a bioactive formulation that includes a composition prepared by culturing cells of a first cell line and a second cell line in a first and a second culture medium, wherein the cells secrete extracellular products into the respective culture medium so that a first conditioned culture medium and a second conditioned culture medium are respectively formed; optionally culturing cells of a third cell line in a third culture medium wherein the cells secrete extracellular products into the culture medium so that a third conditioned culture medium is formed; separating the first, second, and optionally third conditioned culture media from the respective cultured cells; and combining the first and the second conditioned culture media, and optionally the third conditioned culture medium, to form the bioactive composition. In the bioactive formulation according to this aspect, the first, second, and optionally third cell lines can be different from one another and are each selected from the group consisting of an adipose-derived stem cell (ADSC) line, a non-adipose mesenchymal stem cell line, a fibroblast cell line, a hair dermal papilla (HDP) cell line, and a limbal stem cell line. In some particular alternatives of this aspect, implementations of the method provided herein can include one or more of the following features. The first cell line, in some particular alternatives, is an ADSC line. In some particular alternatives, the first cell line is an epithelial stem cell line. In some alternatives, the second cell line is a fibroblast cell line. In some alternatives, the bioactive composition includes conditioned culture medium from a third cell line. In some particular alternatives, the third cell line is a limbal cell line. In some other particular alternatives, the third cell line is an HDP cell line. In yet some other alternatives, at least one of the cell lines is human cell line.

In a further aspect, the present disclosure provides a method for treating an eye condition in a subject in need thereof comprising administering to a subject a therapeutically effective amount of a bioactive formulation disclosed herein. The administering of the method, in some particular alternatives, includes topical administration of the bioactive formulation to an eye of the subject via a carrier vehicle, such as a carrier vehicle selected from the group consisting of a liquid drop, a liquid wash, an ointment, a cream, a gel, a powder, a salve, a lotion, a foam, a spray, and a liposome. In some alternatives, the bioactive is administered topically to the ocular surface or the immediate vicinity of an eye of the subject. In some alternatives, the administering of the method disclosed herein includes infusion of the bioactive formulation to an eye of the subject via a device, such as a device selected from the group consisting of a pump-catheter system, a continuous or selective release device or material, and a contact lens. Alternatively or in addition, according to some alternatives, the administering of the method disclosed herein is via a sustained release insert or implant, subconjunctival injection, intraocular injection, periocular injection, retrobulbar injection, or intracameral injection. In some alternatives, the eye condition results at least in part from aqueous or evaporative dry eye disease, androgen deficiency, allergy, hyperosmolarity, keratoconjunctivitis sicca (KCS), meibomian gland disease, estrogen replacement therapy, refractive surgery, LASIK, corneal transplant, corneal ulcer, reduced tear film breakup time, compromised tear film, allergy, ocular surface disorders, increased protease levels in the tear film and at the ocular surface, chronic inflammation, Sjogren's syndrome, or a combination of any thereof. In some particular alternatives, the bioactive composition disclosed herein is suitable for treatment of keratoconjunctivitis sicca (KCS) otherwise referred to as "dry eye". In some alternatives of this and other aspects of the disclosure, the bioactive composition further includes a thickening agent. In some alternatives, the thickening agent includes cellulosic material, or a polymer. In some alternatives, the bioactive composition can be further combined with an aqueous solution to form an ophthalmic composition for the treatment of KSC.

In some alternatives, the method includes topically administering the bioactive formulation disclosed herein together with one or more ophthalmically acceptable agents, such as an agent selected from the group consisting of a demulcent, an excipient, an astringent, a vasoconstrictor, an emollient, a preservative, a vitamin such as vitamin A, and an electrolyte salt.

In some alternatives, the bioactive compositions disclosed herein are formulated to protect an ocular surface from dryness, absorb shear forces of the blink, as well as to assist gel forming mucins in maintaining their viscoelastic properties and ensuring structure and stability of the tear film.

In one aspect, some alternatives of the present disclosure relate to a method of treating a hair condition in a subject. The method includes administering to the subject a therapeutically effective amount of a bioactive formulation disclosed herein, so that the subject exhibits an improved stimulation of hair growth. In some alternatives, the hair condition to be treated is selected from the group consisting of pattern baldness, alopecia caused by chemotherapy, hair thinning due to aging, illness, stress, traction alopecia, and genetic disorders. In some alternatives, the subject exhibits an improved stimulation of hair growth at a body area, such as at the scalp, back, beard, eyebrows, lashes, leg, arm, pubic region, or a combination of any thereof. In some alternatives, the hair growth is due to thickened hair sheath diameter, increased hair diameter, increased rate of growth in hair length, increased thickness, differentiation of quiescent hair follicles into more mature forms, the appearance of proliferation of new hair follicle, or a combination of any thereof. In some alternatives of this and other aspects of the disclosure, bioactive formulation is administered topically. In some alternatives, bioactive formulation is administered transdermally. In some alternatives, the bioactive formulation is administered in a suitable form, such as in the form of a lotion, a gel, an ointment, a cream, a powder, a salve, a foam, a spray, an exosome, or a liposome.

In some alternatives, also disclosed are bioactive compositions for the treatment of certain diseases, and in a general alternative a composition comprises a therapeutic amount of stem cell released molecules (SRM's) including at least one of: growth factors, cytokines, anti-oxidants, micro-RNA, and mucins; and a carrier for suspending the stem cell released molecules in a solution for delivery, the carrier adapted for topical, oral, injectable, or other forms of delivery of the SRM's to a targeted delivery site, wherein the composition is adapted to stimulate cytogenesis, cytoprotection, immune modulation, and pain relief within tissue adjacent to the targeted delivery site.

The foregoing summary is illustrative only and is not intended to be in any way limiting. In addition to the illustrative aspects, alternatives, and features described above, further aspects, alternatives, objects and features of the invention will become fully apparent from the drawings and the following detailed description and the claims.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several alternatives in accordance with the disclosure and are not to be considered limiting of its scope; the disclosure will be described with additional specificity and detail through use of the accompanying drawings.

DETAILED DESCRIPTION

Figure 1:
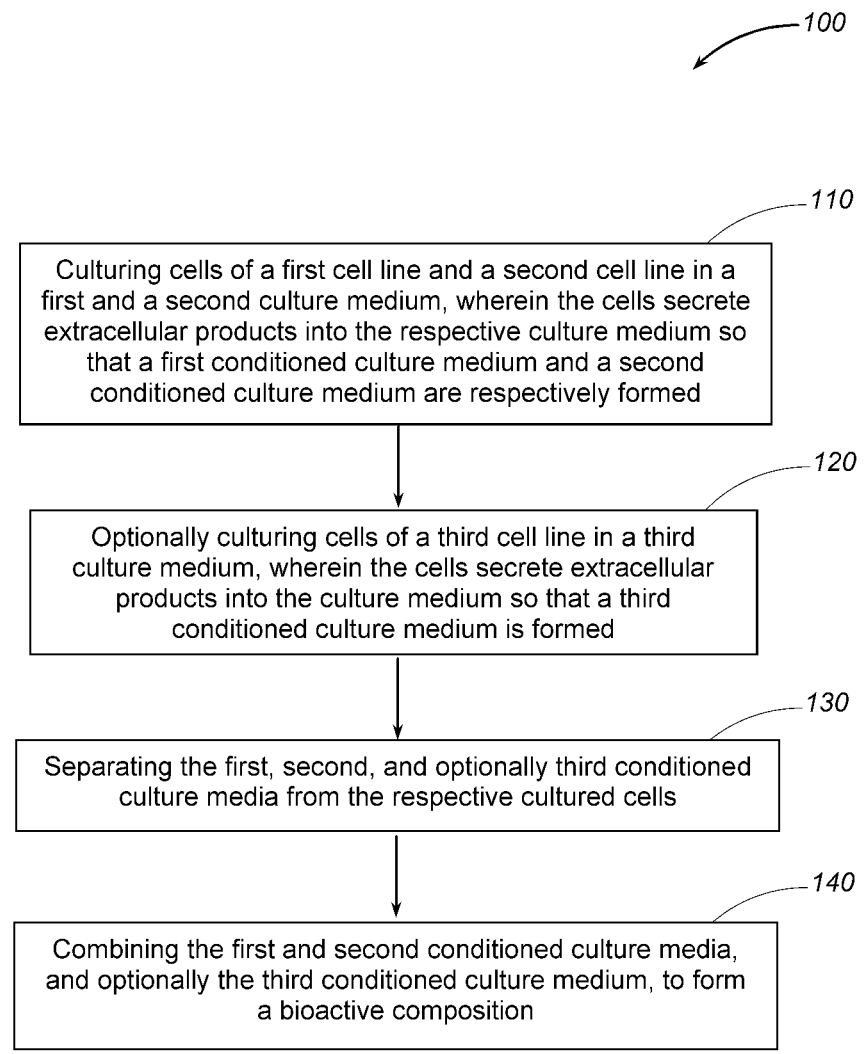
FIG. 1 is a flow diagram illustrating a non-limiting example of a method for making a bioactive composition according to some alternatives of the present disclosure, wherein appropriate amounts of individual culture media that have been conditioned by cultured cells of a first cell line, a second cell lines, and optionally a third cell line are combined to form a bioactive composition.

The present disclosure generally describes bioactive compositions and formulation as well as methods for making and using same, and particularly to bioactive compositions including culture media that have been conditioned by culturing two or more eukaryotic cell types, and each contains bioactive substances that can be defined or undefined. The cells are preferably mammalian cells, most preferably human. In some alternatives, culture media that are conditioned by cells and tissue cultures as disclosed herein contain a variety of naturally secreted proteins, such as biologically active growth factors. In some alternatives, the present disclosure also relates to novel compositions comprising products derived from the conditioned cell media and uses for these compositions. The disclosure further relates to methods for treating various disease and health conditions, such as eye conditions and hair conditions. Further provided, in some alternatives, are kits that include a bioactive composition or formulation disclosed herein.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

The singular form "a", "an", and "the" include plural references unless the context clearly dictates otherwise. For example, the term "a cell" includes one or more cells, including mixtures thereof "A and/or B" is used herein to include all of the following alternatives: "A", "B", "A or B", and "A and B".

"About" means either within plus or minus 10% of the provided value, or rounded to the nearest significant figure, in all cases inclusive of the provided value. Where ranges are provided, they are inclusive of the boundary values.

The terms "administration" and "administering" as used herein refer to the delivery of a bioactive composition or formulation by an administration route including, but not limited to, intravenous, intra-arterial, intramuscular, intraperitoneal, subcutaneous, intramuscular, topically, or combinations thereof.

The terms "bioactive composition" and "bioactive formulation", as used herein, are intended to mean a composition, formulation, product, or ingredient that is bioactive and is prepared from the conditioned culture media disclosed herein. For example, a bioactive composition can be a cosmetic composition, a medicinal composition, a neutraceutical composition, or a pharmaceutical composition. While the focus of preferred alternatives is on cosmetic products and pharmaceutical formulations, particularly eye care products and hair treatment ingredients, it should be understood that the compositions and methods of the present disclosure are also useful for processing any composition, formulations, products, or ingredients comprising a bioactive component, including foods and medical products for administration orally, topically, transdermally, or parenterally. It should also be understood that in some alternatives the bioactive composition will be an ingredient for incorporation into other compositions.

The term "cell line" as used herein refers to one or more generations of cells which are derived from a clonal cell. The term "clone," or "clonal cell," refers to a single cell which is expanded to produce an isolated population of phenotypically similar cells (i.e. a "clonal cell population").

The terms "conditioned culture medium" and "conditioned cell medium" are used interchangeably and refer to a culture medium in which a specific cell or population of cells have been cultured in, and then optionally removed. While the cells were cultured in the medium, they secrete cellular factors that include, but are not limited to hormones, cytokines, extracellular matrix (ECM), metabolites, proteins, vesicles, exosomes, microRNAs, antibodies, and granules. The medium comprising the cellular factors is the conditioned medium.

The term "confluence," as used herein refers to a state of growth of mammalian cells at which cells have proliferated to an extent that cells are observed to touch (thereby "becoming confluent"). Confluence is thus a relative assessment of cell density, e.g., on the surface of a plate. Less-relative measures of cell density can also be used to assess confluence, including, e.g., cell counting (e.g., in certain alternatives, cells are grown to confluence such that approximately $10^6$ cells are present per mL in culture, e.g., involving growth of cells in a 10 cm plate in 10 mL culture medium).

As used herein, the term "epithelium" is herein defined as membranous tissue composed of one or more layers of cells separated by very little intercellular substance and forming the covering of most internal and external surfaces of the body and its organs comprising one or more epithelial cell types. The term "epithelial stem cell" is herein defined as a stem cell being capable of differentiation into a variety of epithelial cell types.

The term "fibroblast" as used herein refers to a type of cell encountered in many tissues of the body including connective tissue and that can be derived using standard cell culture methods. For example, fibroblasts can be generated from adult and fetal tissues including blood, bone marrow, cord blood and placenta. In one alternative, the fibroblast is a dermal fibroblast. The term "dermal fibroblast" as used herein refers to fibroblasts isolated from skin of any animal, such as a human. In one alternative, the animal is an adult. In another alternative, the fibroblast has been cryopreserved.

The term "limbus", as used herein, is defined as a distinctive border or edge, such as the junction between the cornea and sclera of the eyeball comprising one or more limbal cell types. The term "limbal stem cell" is herein defined as a stem cell capable of differentiation into a variety of limbal cell types.

As used herein, the term "mesenchymal stem cell" refers to mesodermal germ lineage cells which may or may not be differentiated. The mesenchymal cells that are suitable for the compositions and methods disclosed herein include cells at all stages of differentiation beginning with multipotent mesenchymal stem cells, down to fully differentiated terminal cells.

As used herein, the term "pharmaceutically acceptable carrier", which may be used interchangeably with the term "biologically compatible carrier", refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

As used herein, a "therapeutically effective amount," "therapeutically effective concentration" or "therapeutically effective dose" is an amount which, as compared to a corresponding subject who has not received such amount, results in improved treatment, healing, prevention, or amelioration of a disease, disorder, or side effect, or a decrease in the rate of advancement of a disease or disorder.

This amount will vary depending upon a variety of factors, including but not limited to the characteristics of the bioactive compositions and formulations disclosed herein (including activity, pharmacokinetics, pharmacodynamics, and bioavailability thereof), the physiological condition of the subject treated (including age, sex, disease type and stage, general physical condition, responsiveness to a given dosage, and type of medication) or cells, the nature of the pharmaceutically acceptable carrier or carriers in the formulation, and the route of administration. Further, an effective or therapeutically effective amount may vary depending on whether the one or more bioactive compositions and formulations disclosed herein is administered alone or in combination with other drug(s), other therapy/therapies or other therapeutic method(s) or modality/modalities. One skilled in the clinical and pharmacological arts will be able to determine an effective amount or therapeutically effective amount through routine experimentation, namely by monitoring a cell's or subject's response to administration of the one or more bioactive compositions and formulations disclosed herein and adjusting the dosage accordingly. A typical dosage may range from about 0.1 mg/kg to about 100 mg/kg or more, depending on the factors mentioned above. In other alternatives, the dosage may range from about 0.1 mg/kg to about 100 mg/kg; or about 1 mg/kg to about 100 mg/kg; or about 5 mg/kg up to about 100 mg/kg. For topical applications such as, for example, treatment of various hair conditions, according to some alternatives disclosed herein, suitable dosage may range from about 1 mg/kg to about 10 g/kg; or about 10 mg/kg to about 1 g/kg; or about 50 mg/kg up to about 10 g/kg. Additional guidance with regard to this aspect can be found in, for example, Remington: *The Science and Practice of Pharmacy*, $21^{st}$ Edition, Univ. of Sciences in Philadelphia (USIP), Lippincott Williams & Wilkins, Philadelphia, Pa., 2005, which is hereby incorporated by reference as if fully set forth herein for additional guidance for determining a therapeutically effective amount.

A "stem cell" as used herein refers to an undifferentiated cell which is capable of remaining in an undifferentiated state (e.g., pluripotent or multipotent stem cell) for extended periods of time in culture until induced to differentiate into other cell types having a particular, specialized function (e.g., fully differentiated cells). Stem cells have varying degrees of potency. The phrase "pluripotent stem cells" encompasses embryonic stem cells (ESCs) and induced pluripotent stem cells (iPS). The stem cells are typically mammalian pluripotent cells, such as for example human pluripotent stem cells.

The term "stem cell released molecules" or SRM's is a generic term for a group of chemicals, proteins, microRNAs, and other molecules secreted by cultured stem cells and the other cell types disclosed herein, and can be found in the medium wherein the cells are cultured and thus such a medium is called conditioned culture medium. Thus, SRM can comprise mucins, cytokines, and growth factors. The term "mucin" as used herein, is intended to refer to any of a group of protein-containing glycoconjugates with high sialic acid or sulfated polysaccharide content that compose the chief constituent of mucus. The term "interleukin" is herein used as a generic term for a group of multifunctional cytokines that are produced by a variety of lymphoid and nonlymphoid cells and whose effects occur at least partly within the lymphopoietic system. The term "cytokine", as used herein, is defined as a generic term for non-antibody proteins released by one cell population on contact with specific antigen, which act as intercellular mediators, as in the generation of an immune response. In some alternatives, the compositions disclosed herein may include SRMs or conditioned media containing SRMs secreted by at least two cell lines.

The term "subject" as used herein refers to animals, including mammals, preferably humans, who are treated with the bioactive compositions and formulations and/or in accordance with the methods described herein. The term "mammal", according to some alternatives of the methods of treatment disclosed herein, includes both humans and non-humans and include but is not limited to humans, non-human primates, canines, felines, murines, bovines, equines, and porcines. As such, as used herein, animals can include domestic and farm animals, zoo animals, sports or pet animals, such as dogs, horses, cats, cattle, pigs, sheep, etc. In some particular alternatives, the term subject refers to domesticated non-mammal animals with canines, felines, fowl, poultry, and small reptiles being the most preferred.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

In some alternatives disclosed herein, a therapeutic composition generally comprises an amount of stem cells and stem cell released molecules (SRM's) being derived from a first cell line by in vitro culture. The stem cells and SRM's are generally cultured in a nutrient medium by way of Petri dishes, flasks, bioreactors, and the like. In some alternatives, cell cultures can be made using two-dimensional or three-dimensional culture technologies. Once sufficient SRM's are produced, the cells and SRM's are suspended in an aqueous solution. A thickening agent, such as a cellulosic material or polymer may be provided for enhancing viscosity of the composition. In this regard, a therapeutic composition can be administered to a patient for moisturizing a tissue region and delivering important bioactive materials such as SRM's for stimulating a healing response in damaged tissue.

In certain alternatives, the bioactive composition disclosed herein can further include an amount of stem cells and SRM's derived from a second cell line, wherein the second cell line is distinct from the first cell line. In this regard, a plurality of stem cells and SRM's can be administered to effectuate a synergistic and emergent healing response in vivo.

In some alternatives, three or more cell lines are provided and cultured to yield respective SRM's, wherein each of the cell lines is distinct from each other.

Many cell lines are commercially available in the art, however each indication should be appropriately matched with one or more targeted cell lines. For example, in an effort to treat keratoconjunctivitis sicca (KCS), otherwise referred to as "dry eye", or "ocular surface disease", a therapeutic composition can include those cells and SRM's which may naturally occur in the tissues relating to and surrounding the eyes, such as the ophthalmic tissues including the cornea, conjunctiva, and other eye tissues. In the case of KCS, a patient requires a healing response in the ophthalmic tissues, and more specifically the tear film adjacent to the corneal scleral tissues, and thus a therapeutic composition can be tailored accordingly.

By way of example, in one alternative includes a therapeutic composition is provided for the treatment of KCS, the composition comprises: an amount of stem cells and SRM's derived from a first cell line, and an amount of stem cells and SRM's derived from a second cell line. The stem cells and SRM's of the first cell line are collectively referred to as a first adjuvant material, while those of the second cell line are referred to as a second adjuvant material. Each of the first and second cell lines individually comprises one of: mesenchymal stem cells, epithelial stem cells, limbal stem cells, or fibroblasts, wherein the first and second cell lines are distinct with respect to each other. The composition further comprises a thickening agent, the thickening agent comprising at least one of: a cellulosic material, or a polymer. The first adjuvant material, second adjuvant material, and thickening agent are further combined in an aqueous solution to form a therapeutic ophthalmic composition for the treatment of KCS. The composition can additionally comprise one or more electrolytes, vitamin A, or preservatives.

In this regard, certain mesenchymal stem cells, epithelial stem cells, limbal stem cells, and fibroblasts tend to naturally occur within human eye tissues. Each of these types of cells is therefore capable of producing one or more SRM's useful in maintaining the integrity and health of the human eye tissue. SRM's may include for example: mucins, cytokines, and growth factors for stimulating a cytogenesis, immune modulation, or repair response in the targeted tissue.

Mucins are a family of high molecular weight, heavily glycosylated proteins (glycoconjugates) produced by epithelial tissues. Mucins' key characteristic is their ability to form gels; therefore they are a key component in most gel-like secretions, serving functions including lubrication, cell signaling, and forming chemical barriers, among others.

Ocular surface mucins are highly glycosylated proteins which provide structure the tear film by binding both to each other and to the aqueous component of the tear film, helping to stabilize the tear film. Mucins are essential for maintaining ocular surface health. In a healthy eye, the concentration of ocular surface mucins is highest near the surface of the globe, and it gradually decreases as the tear/air interface is approached.

Within this gradient, different types of mucins are believed to occupy different positions and perform different functions. For example, secreted mucins, such as MUC4 and MUC7, are produced by the lacrimal gland. These are the smallest mucin molecules in the tear film. Additionally, gel-forming mucins, such as MUC5-AC, are secreted by the goblet cells of the conjunctiva. Like the secreted mucins, gel-forming mucins are dissolved in the tear film, but gel-forming mucins are larger and more interactive with other mucin molecules. Furthermore, membrane-associated mucins, such as MUC1 and MUC16, are even longer molecules that have an intracellular extension serving to anchor them to epithelial cells. These mucins play a key role in protecting the ocular surface, and when these mucins are absent or damaged ocular surface staining results. Other mucins in the tear film include MUC2, among others.

These and other mucins have been produced by in vitro culture of limbal stem cells, and have been further incorporated into various compositions in accordance with alternative embodiments.

Cytokines include immune-modulating agents, such as interleukins and interferons. These agents are capable of soliciting and inducing an immune response in vivo.

In the tear film of the eye, a higher concentration of cytokines, such as interleukin (IL)-2, IL-4, IL-5, IL-6, IL-10, interferon (IFN)-gamma, tumor necrosis factor (TNF)-α, and IL-1β, has been shown to correlate with severity of dry eye syndrome. It is believed that these cytokines are responsible for promoting a healing response in patients with ocular surface disease. Accordingly, these and other related cytokines have been incorporated into various compositions in accordance with certain embodiments. Generally, the cytokines are secreted by limbal stem cells in vitro using a culturing technique. Once produced, the cytokines are suspended in a solution and delivered to the targeted tissue in accordance with various alternatives herein.

Growth factors are naturally occurring substance capable of stimulating cellular growth, proliferation and cellular differentiation. Growth factors generally include proteins and steroid hormones, and are important for regulating a variety of cellular processes.

A number of biologically active growth factors are secreted by the lacrimal gland and distributed via the tears over the ocular surface, where they affect cellular proliferation, migration, differentiation, and survival. Epidermal growth factor release rates have been shown to be significantly lower in eyes with ocular surface diseases than in normal eyes during reflex tearing.

Examples of growth factors include: LIF, VEGF, HGF, SDF, SCF, M-CSF, bFGF, IGFBP, Oncostatin M, MIP1-β, TIMP-2, TGF-β1, TGF-β2, PDGF, EGF, KGF, GM-CSF, HGF, MCP-1, TNFα, FGF-2, Flt-3, PDGF-AA, and TGF-β3.

Keratinocyte growth factor (KGF) and hepatocyte growth factor (HGF), among others, have been obtained by in vitro culture of stem cells and incorporated into therapeutic compositions according to various alternative alternatives.

In various alternatives, stem cells are generally stimulated to induce secretion of targeted SRM's in culture. This is generally accomplished by introducing the cultured cells to certain antigens, cytokines, and other molecules during in vitro processing to simulate a bio-condition. In this regard, certain antigens or other stimulants may stimulate the cultured cells into producing the targeted SRM's. Furthermore, the cells can further differentiate into specific cell types, or matured in vitro by introducing certain antigens, proteins, and other bio-molecules. Throughout the culturing process, the stem cells can be transformed into differentiated or matured cells, and SRM's can be synthesized through one or more simulated bio-conditions in vitro. Thus, the harvested cells can be transformed and new molecules produced through in vitro culturing.

In certain alternatives, cells are manipulated in culture by any of: depleting a culture medium of certain nutrients to replicate a bio-condition; accumulating dead or ablated cells in the nutrient medium; and cell to cell contact to stimulate differentiation and maturation of cells, or other technique known to those having skill in the art.

In certain alternatives, a thickening agent can be incorporated into the composition for increasing viscosity thereof. The thickening agent can be any cellulosic material, such as methyl cellulose, sodium carboxymethyl cellulose, and hydroxypropylmethyl cellulose. Alternatively, certain polymers can be incorporated as thickening agents, such as carboxyvinyl polymer, polyvinyl alcohol, polyvinyl pyrrolidone, polyethylene glycol, and polysorbate 80.

Although certain ophthalmic compositions are described herein, the compositions can be applied to a wide variety of tissue conditions, such as colonitis, diabetic ulcers, among others. Furthermore, although several alternatives provide a composition for topical administration, such as eye drops, gels, and creams, it is within the scope of the disclosure to provide injectable compositions and the like.

In another aspect, certain methods are disclosed for formulation of these compositions, a general method comprising: providing an amount of first stem cells; culturing the first stem cells in vitro such that the first stem cells are stimulated to secrete one or more SRM's; introducing a thickening agent; and suspending the first stem cells, SRM's, and thickening agent in an aqueous solution.

In certain alternatives, a method for formulation of a therapeutic composition further includes the steps of: providing an amount of second stem cells, the second stem cells being distinct from the first stem cells; culturing the second stem cells in vitro such that the second stem cells are stimulated to secrete one or more SRM's; and combining the first and second stem cells and SRM's in a suspension.

FIG. 1 is a flow diagram illustrating a non-limiting example of a method for making a bioactive composition according to some alternatives disclosed herein.

As schematically illustrated in FIG. 1, in some alternatives, method 100 can include one or more functions, actions, or Steps as illustrated by one or more of Steps 110-140.

Method 100 can begin at Step 110, "Culturing cells of a first cell line and a second cell line in a first and a second culture medium, wherein the cells secrete extracellular products into the respective culture medium so that a first conditioned culture medium and a second conditioned culture medium are respectively formed." Step 110 can be followed by Step 120, "Optionally culturing cells of a third cell line in a third culture medium, wherein the cells secrete extracellular products into the culture medium so that a third conditioned culture medium is formed." Step 120 can be followed by Step 130, "Separating the first, second, and optionally third conditioned culture media from the respective cultured cells." Step 130 can be followed by Step 140, "Combining the first and second conditioned culture media, and optionally the third conditioned culture medium, to form a bioactive composition."

In FIG. 1, Steps 110-140 are illustrated as being performed sequentially with Step 110 first and Step 140 last. It will be appreciated, however, by those skilled in the art that these Steps can be reordered, combined, and/or divided into additional or different Steps as appropriate to suit particular alternatives. For example, additional Steps can be added before, during or after one or more of Steps 110-140. For example, an additional Step, "Formulating said bioactive composition to form an aerosol, a cream, a dispersion, an emulsion, a film, a foam, a gel, a liquid, a lotion, a lyophilisate, a mousse, an ointment, a powder, a solid, a spray, a suspension," can be optionally included after Step 140. In some particular alternatives, cells of the first, second, and/or third cell lines have been passaged multiple times prior to being subjected to Step 110 and/or 120. Further, in some alternatives, one or more of the foregoing Steps can be performed at the same time. For example, Steps 110 and 120 can be performed at the same time.

At Step 110, "Culturing cells of a first cell line and a second cell line in a first and a second culture medium, wherein the cells secrete extracellular products into the respective culture medium so that a first conditioned culture medium and a second conditioned culture medium are respectively formed," the first and second cell line are different from one another and can be each selected from a large number of cell lines, such as an adipose-derived stem cell (ADSC) line, a non-adipose mesenchymal stem cell line, a bone marrow stem cell line, a fibroblast cell line, a hair dermal papilla (HDP) cell line, and a limbal stem cell line. In some alternatives, the first cell line can be an ADSC line. In some alternatives, the second cell line is a fibroblast cell line.

At Step 120, "Optionally culturing cells of a third cell line in a third culture medium, wherein the cells secrete extracellular products into the culture medium so that a third conditioned culture medium is formed," the third cell line can be different from the first and second cell lines and can be each selected from a large number of cell lines, such as an adipose-derived stem cell (ADSC) line, a non-adipose mesenchymal stem cell line, a bone marrow stem cell line, a fibroblast cell line, a hair dermal papilla (HDP) cell line, and a limbal stem cell line. In some alternatives, the third cell line can be a limbal stem cell line. In some alternatives, the third cell line can be an HDP cell line.

In some alternatives disclosed herein, each of the culturing operations at Steps 110 and 120 can be performed for at least 2 days, at least 5 days, at least 7 days, at least 8 days, or at least 10 days. In some alternatives, each of the culturing operations at Steps 110 and 120 can be carried out until the culture reaches at least 85%, at least 90%, at least 95%, or at least 98% cell confluence. In some alternatives, the cells of at least one of the cell lines have been passaged multiple times prior to being subjected to Steps 110 and/or 120 to produce the conditioned culture media. In some particular alternatives, the cells of at least one of the cell lines have been passaged at least 2, 3, 4, 5, 6, 7, 8, 9, or 10 times to produce the conditioned culture media. In certain alternatives, the cells of at least one of the cell lines are passaged after reaching at least 85%, at least 90%, at least 95%, or at least 98% cell confluence.

At Step 140, in some other alternatives, the bioactive composition can include a ratio of the first conditioned culture medium to the second conditioned culture medium of between about 1:10 to about 10:1. In some particular alternatives, the ratio of the first conditioned culture medium to the second conditioned culture medium is about 1:1.

In some alternatives, an additional Step, "Formulating said bioactive composition to form an aerosol, a cream, a dispersion, an emulsion, a film, a foam, a gel, a liquid, a lotion, a lyophilisate, a mousse, an ointment, a powder, a solid, a spray, a suspension," can be included after Step 140. In some alternatives, the bioactive composition is suitable for a cosmetic application, a medicinal application, a neutraceutical application, or a pharmaceutical application.

Figure 2:
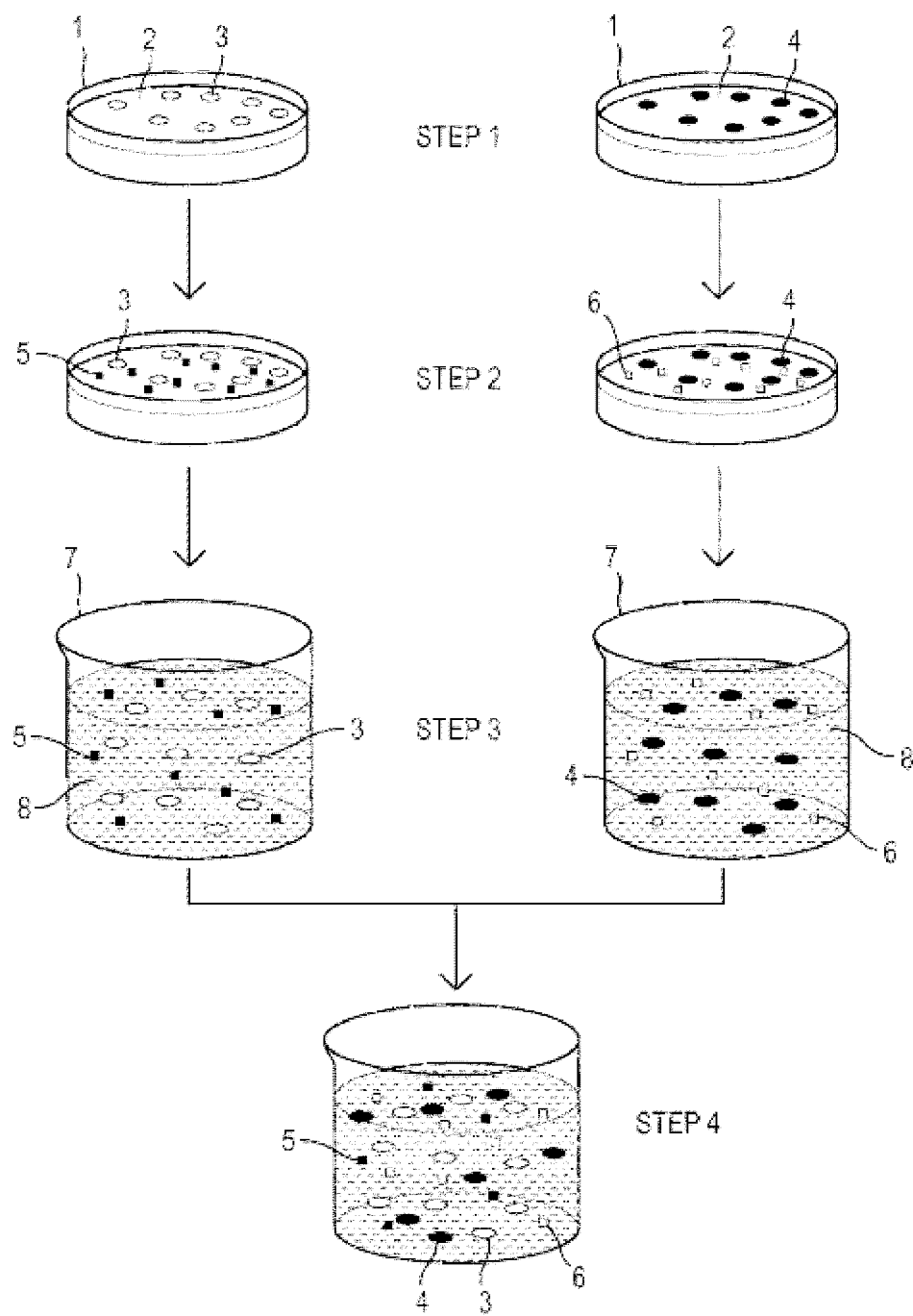
FIG. 2 illustrates a non-limiting example of a method for making a bioactive composition in accordance with some alternatives of the present disclosure, wherein an amount of cells and secreted extracellular products derived from a first cell line are combined with an amount of cells and secreted extracellular products derived from a second cell line to form a bioactive composition.

FIG. 2 illustrates a non-limiting example of a method for making a bioactive composition. As schematically illustrated in FIG. 2, in some alternatives, the method includes the steps of (Step 1) providing cells in a cell culture receptacle 1. The term "receptacle" as used herein is intended to include any means suitable for containing and/or growing a cell culture. As such, the term "cell culture receptacle", as used herein, includes but is not limited to Petri dishes, test tubes, cell culture flasks, multi-well plates, microwell plates, cell culture vessels, bioreactors, and the like. Cells of a first cell line 3 are grown in a suitable first culture medium 2 in a first receptacle. Cells of a second cell line 4 are grown in a suitable second culture medium 2 in a second receptacle. The culture medium may be the same or different for cells of the first cell line 3 and the second cell line 4. In some alternatives, cells of the first and second cell lines are cultured separately in different culture media. In some alternatives, cells of the first cell line 3 and second cell line 4 are cultured in the same growth medium. In some alternatives, cells of the first cell line 3 and second cell line 4 are cultured under the same growth conditions. In some alternatives, cells of the first cell line 3 and second cell line 4 are cultured under different growth conditions. (Step 1) can be followed by (Step 2), culturing the cells of the first and second cell lines wherein the cells secrete extracellular products 5; 6 into the respective culture medium so that a first conditioned culture medium and a second conditioned culture medium are respectively formed. (Step 2) can be followed by (Step 3), suspending the cultured cells and secreted extracellular products of each cell line in a solution 8. (Step 3) can be followed by (Step 4), combining the cultured cells and secreted extracellular products derived from the two cell lines to formulate a bioactive composition comprising an amount of cells of the first cell line 3, an amount of cells of the second cell line 4, an amount of first secrete extracellular products 5, and amount of second secrete extracellular products 6, and a solution 8.

In FIG. 2, Steps 1-4 are illustrated as being performed sequentially with Step 1 first and Step 4 last. It will be appreciated however that these Steps can be reordered, combined, and/or divided into additional or different Steps as appropriate to suit particular alternatives. For example, additional Steps can be added before, during or after one or more of Steps 1-4. For example, in some alternatives, an additional (i.e. Step 5), "formulating said conditioned culture medium or said bioactive composition to form an aerosol, a cream, a dispersion, an emulsion, a film, a foam, a gel, a liquid, a lotion, a lyophilisate, a mousse, an ointment, a powder, a solid, a spray, a suspension," can be optionally included after Step 4. In another example, according to some alternatives disclosed herein, cells of a third cell line are cultured in a third culture medium, wherein the cells secrete extracellular products into the culture medium so that a third conditioned culture medium is formed. In some alternatives, one or more of the foregoing Steps can be performed at the same time.

Cell Lines

According to some alternatives, the conditioned culture media described herein can be conditioned by specific cell lines. Preferably, each of the cell lines is substantially free of other cell types and extracellular matrix material, more preferably, the cell line if completely free of such other cell types and matrix materials. The cell line is derived from any animals, preferably from a primate, and more preferably from a higher primate (such as a baboon or ape), and most preferably from human. In some alternatives, the cell line will be derived from a human tissue, which can be an adipose or non-adipose tissue. Suitable cell lines for the methods and compositions disclosed herein include stromal cells, parenchymal cells, mesenchymal stem cells, liver reserve cells, neural stem cells, pancreatic stem cells, adipose-derived stem cells (ADSC), non-adipose mesenchymal stem cells, fibroblast cells, hair dermal papilla (HDP) cells, limbal stem cells, and/or embryonic stem cells. Further, mesenchymal stem cells (lineage committed or uncommitted progenitor cells) are advantageous "stromal" cells for use in some particular alternatives of the compositions and methods disclosed herein. The cells may differentiate into osteocytes, fibroblasts of the tendons and ligaments, marrow stromal cells, adipocytes and other cells of connective tissue, chondrocytes, depending of course, on endogens or supplemented growth and regulatory factors and other factors including prostaglandin, interleukins and naturally-occurring chalones which reversibly inhibit and/or regulate cell proliferation and/or differentiation. In some alternatives, suitable for the compositions and methods disclosed herein are stromal cells, parenchymal cells, mesenchymal stem cells (lineage committed or uncommitted progenitor cells), liver reserve cells, neural stem cells, pancreatic stem cells, and/or embryonic stem cells. In some alternatives, suitable cells may include, but are not limited to, bone marrow, skin, liver, pancreas, kidney, neurological tissue, adrenal gland, mucosal epithelium, and smooth muscle.

Fibroblasts and fibroblast-like cells and other cells and/or elements that comprise the stroma may be fetal or adult in origin, and may be derived from convenient sources such as skin, liver, pancreas, mucosa, arteries, veins, umbilical cord, and placental tissues, etc. Such tissues and/or organs can be obtained by appropriate biopsy or upon autopsy. Additionally, cadaver organs may be used to provide a generous supply of stromal cells and elements.

Embryonic stem cells and/or other elements that comprise the stroma may be isolated using methods known in the art. For instance, human embryonic stem cell populations and methods for isolating and using these cells have been reported in Smith, Curr. Biol. 8:R802-804 (1998), and Keller et al., Nature Med., 5:151-152 (1999). Further, human embryonic stem cell have been isolated from blastocytes (Thomason et al., Science 282:1145-1147, 1988), and from primordial germ cells (Shamblatt et al., PNAS 95:13726-1373, 1998). The isolation and culture of mesenchymal stem cells are also known in the art. See William et al., Am Surg. 65:22-26 (1999), and Mackay et al., Tissue Eng. 4:415-428 (1988). Additionally, neural stem cells may be isolated in the manner described in ax et al., Nature Biotechnol., 16:1033-1039 (1998); and Frisen et al., Cell. Mol. Life Sci., 54:935-945 (1998).

In some particular alternatives, the cells may be cultured in any manner known in the art including in monolayer, cell suspension, beads or in three-dimensions and by any means (i.e., culture dish, roller bottle, a continuous flow system, etc.). Methods of cell and tissue culturing are well known in the art, and are described, for example, in *Cell & Tissue Culture: Laboratory Procedures*, John Wiley & Sons Ltd., 1996; and *Culture of Animal Cells: A Manual of Basic Techniques*, Freshney 1987.

Preferably, the cell lines utilized in the bioactive compositions and methods disclosed herein are carefully screened for human and animal pathogens. Depending upon the application, such screening may be of critical importance where only pathogen free cells are acceptable (e.g., for wound healing, food additives, etc.) Methods of screening for pathogens are well known in the art.

In some alternatives of the compositions and methods disclosed herein, the cells can be genetically engineered to express a target gene product which is biologically active which provides a chosen biological function, or acts as a reporter of a chosen physiological condition, or augments deficient or defective expression of a gene product, or provides an anti-viral, anti-bacterial, anti-microbial, or anti-cancer activity. In accordance with some alternatives, the target gene product may be a peptide or protein, such as an enzyme, hormone, cytokine, antigen, or antibody, a regulatory protein, such as a transcription factor or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may upregulate an endogenous protein, introduce a new protein or regulate ion concentration by expressing a heterologous ion channel or altering endogenous ion channel function. Other examples include, but are not limited to engineered tissues that express gene products which are delivered systemically (e.g., secreted gene products such as proteins including Factor VIII, Factor IX, growth factors, hormones, enkaphalins, and neurotransmitters). Methods that are useful to genetically engineer the cells that can be used to condition the culture media included in the bioactive compositions and formulation disclosed herein are well-known in the art.

Cell Culture Media and Supplements

Culture medium in vitro culture represents microenvironment in vivo conditions and may determine cell fate and thus cell secretion. Therefore, the same type of cells may secrete different level of growth factors when are cultured in different media. A number of basal cell culture media formulations are known in the literature and many are commercially available. Pre-conditioned cell culture medium can be any cell culture medium which adequately addresses the nutritional needs of the cells being cultured. Examples of basal cell media include, but are not limited to Complete MesenPRO RS™ Medium, Dulbecco's Modified Eagle's Medium (DMEM), Mesenchymal Stem Cell Medium (MSMC), Ham's F12, RPMI 1640, Iscove's, McCoy's, αMEM, DMEM/F12, M199, EBM2, EGM-2, In Vivo 15, or chemically defined media, and other media formulations readily apparent to those skilled in the art, including those found in *Methods For Preparation of Media, Supplements and Substrate For Serum-Free Animal Cell Culture*, Alan R. Liss, New York (1984) and *Cell & Tissue Culture: Laboratory Procedures*, John Wiley & Sons Ltd., 1996.

In some alternatives, the same type of cell can be cultured in different kinds of basal medium. Additionally, the appropriate concentrations of the ingredients in a given basal growth medium are well known to one of ordinary skill in the art. See, for example, *Methods For Preparation Of Media, Supplements and Substrate for Serum-free Animal Cell Cultures*, supra. The ingredients include amino-acids (both D and/or L-amino acids) such as glutamine, alanine, arginine, asparagine, cystine, glutamic acid, glycine, histidine, isoleucine, leucine, lysine, methionine, phenylalanine, proline, serine, threonine, tryptophan, tyrosine, and valine and their derivatives; acid soluble subgroups such as thiamine, ascorbic acid, ferric compounds, ferrous compounds, purines, glutathione and monobasic sodium phosphates.

Additional ingredients such as vitamins, growth and attachment factors, proteins and the like, can be selected by those of skill in the art in accordance with any particular need. Particularly suitable ingredients, in some alternatives, include sugars, deoxyribose, ribose, nucleosides, water soluble vitamins, riboflavin, salts, trace metals, lipids, acetate salts, phosphate salts, HEPES, phenol red, pyruvate salts and buffers.

Other ingredients often used in media formulations include fat soluble vitamins (including A, D, E and K) steroids and their derivatives, cholesterol, fatty acids and lipids Tween 80, 2-mercaptoethanol pyramidines as well as a variety of supplements including serum (calf, fetal, horse, etc.), proteins (insulin, growth factors, hormones, transferrin, etc.), antibiotics (amphotericin B, gentamicin, penicillin, streptomycin, etc.), whole egg ultra-filtrate, and attachment factors (fibronectins, collagens, laminins, tenascins, vitronectins, etc.).

In some particular alternatives of the method of making a bioactive composition disclosed herein, each of the cell lines can be cultured for at least 2 days, at least 5 days, at least 7 days, at least 8 days, or at least 10 days to form the respective conditioned culture medium. In some alternatives, each of the culturing steps is carried out until said culture reaches at least 85%, at least 90%, at least 95%, or at least 98% cell confluence. In some alternatives, the cells of at least one of the cell lines have been passaged multiple times to produce the conditioned culture media. In some particular alternatives, the cells of at least one of the cell lines can be passaged at least 2, 3, 4, 5, 6, 7, 8, 9, or 10 times to form the conditioned culture media. In some particular alternatives, when one of the cell lines is a human hair dermal papilla (hHDP) cell line, the hHDP cells can be passaged 2, 3, or 4 times to form the conditioned culture media. In certain alternatives, the cells of at least one of the cell lines are passaged after reaching at least 85%, at least 90%, at least 95%, or at least 98% cell confluence. In some other alternatives, the bioactive composition disclosed herein includes a ratio of the first conditioned culture medium to the second conditioned culture medium of between about 1:10 to about 10:1. In some particular alternatives, the bioactive composition disclosed herein includes a ratio of the first conditioned culture medium to the second conditioned culture medium of about 1:1. In some particular alternatives, the bioactive composition disclosed herein includes the first, second, and third conditioned culture media each in the amounts of 33.3% v/v of the total volume.

Recovery of the Conditioned Culture Media

According to some aspects and alternatives of the present disclosure, the cells can be cultured by generally any means, methods and systems known in the art. Preferably, the cells are cultured in an environment which enables aseptic processing and handling. In some alternatives, the culture media be conditioned in a manner allowing for large scale growth (and yielding large scale conditioned media) using, for example, an apparatus for aseptic large scale culturing.

In some alternatives, cultured cells can be separated from the culture media in which they have been grown or maintained by one or more methods known in the art, for example using cell settling and decant, batch, continuous centrifugation, and/or microfiltration. The cell-free conditioned culture media obtained may be further processed to concentrate or reduce one or more factors or components, for example using filtration, diafiltration or chromatographic purification.

In some alternatives, following removal of the cultured cells from the conditioned medium, it may be necessary to further process the resulting supernatant. Such processing can include, but are not limited to, concentration by a water flux filtration device or by diafiltration, or by using any of the methods described in *Cell & Tissue Culture: Laboratory Procedures*, supra. Additionally, the conditioned medium can be further processed for product isolation and purification to remove unwanted substances and compounds, such as proteases. The methods used for product isolation and purification so that optimal biological activity is maintained will be readily apparent to one of ordinary skill in the art. For example, it may be desirous to purify a secreted cellular growth factor, regulatory factor, peptide hormone, antibody, etc. Such methods include, but are not limited to, gel chromatography (using matrices such as Sephadex™) ion exchange, metal chelate affinity chromatography with an insoluble matrix such as cross-linked agarose, HPLC purification, and hydrophobic interaction chromatography of the conditioned media. Such techniques are known, many of which are described in greater detail in, e.g., *Cell & Tissue Culture; Laboratory Procedures*, supra. Further, depending upon the desired application of the conditioned medium, and/or products derived thereof, appropriate measures can be taken to maintain sterility. Alternatively or in addition, sterilization may be necessary and can be accomplished by methods known to one of ordinary skill in the art, such as, for example, heat and/or filter sterilization with care taken to preserve the desired biological activity.

Bioactive Formulations

As described above, the bioactive compositions disclosed herein contain conditioned culture media that include a variety of useful pharmaceutical factors and components such as growth factors, regulatory factors, peptide hormones, antibodies, and are therefore useful for a variety of applications, such as cosmetic applications, medicinal applications, neutraceutical applications, and pharmaceutical applications.

It will be appreciated that other compounds and products may be added to the presently disclosed bioactive formulations, including but are not limited to, antibiotics, antiseptics, antimicrobial substances, antivirals, antifungals, bacteriostatic, steroids, analgesics, antitumor drugs, investigational drugs or any compounds which would result in a complementary or synergistic combination with the factors in the presently disclosed conditioned culture media. As discussed herein, the cells are cultured, and the conditioned culture media are recovered and combined under aseptic conditions. Additionally, the bioactive compositions and formulations can be tested for pathogens. In instances where sterilization is needed, it is preferably performed in a manner which minimally affects the desired biological activity as described herein.

In some particular alternatives, the conditioned culture media can be further processed to concentrate or reduce one or more factors or components contained within the media, for example, enrichment of a growth factor using immunoaffinity chromatography or, conversely, removal of a less desirable component, for any given application as described herein. In some alternatives, the bioactive formulations are made from media conditioned by two or more different cell lines. In some alternatives, bioactive formulations are made from media conditioned by three or more, four or more, five or more different cell lines. Typically, the cultured cells produce a multitude of growth factors and proteins that are subsequently secreted into the media at physiological ratios and concentrations. The conditioned culture media, therefore, provide a unique combination of factors and specified ratios that closely represent those found in vivo. In some alternatives, prior to combining the conditioned culture media to form a bioactive composition, it is preferable to remove cellular debris or other particular matter as well as proteases, lactic acid and other components potentially detrimental to cell growth. In other alternatives, the bioactive compositions can also include cells that have been cultured (see, e.g. FIG. 2).

In some alternatives, the bioactive compositions disclosed herein may be formulated into pharmaceutical formulations in the form of liquid drops such as eye drops, nose drops, ear drops; liquid washes, creams, ointments, injectables, gels such as hydrogels, powders, salves, lotions, foams, sprays, tablets, capsules, skin patches, inhalers, exosomes, liposomes, or into any other appropriate formulations known to one of skill in the art. In some alternatives, the bioactive compositions disclosed herein can be formulated with a pharmaceutically acceptable carrier as a vehicle for internal administration. In some alternatives, the bioactive compositions may be formulated as a sterile solution or suspension, in suitable vehicles, many of which are well known in the art. In some particular alternatives, the bioactive compositions disclosed herein can be processed and formulated for a number of applications such as for treating various eye conditions or hair conditions. Information with regard to suitable formulations and additional carriers can be found in, e.g., Remington *"The Science and Practice of Pharmacy"*

(20th Ed., Lippincott Williams & Wilkins, Baltimore Md.), the teachings of which are incorporated by reference in their entirety herein.

For injectable formulations, the vehicle may be chosen from those known in the art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutically acceptable vehicles. The concentration of bioactive composition may be adjusted, the pH of the solution buffered and the isotonicity adjusted to be compatible with intravenous injection, as is well known in the art.

Suitable oral formulations include tablets, capsules, troches, pills, wafers, chewing gums, lozenges, aqueous solutions or suspensions, oily suspensions, syrups, elixirs, or dispersible powders or granules, and the like and may be made in any way known in the art. In some alternatives, oral administration the pharmaceutical compositions may take the form of, for example, tablets or capsules prepared by conventional means with pharmaceutically acceptable excipients such as binding agents (e.g., pre-gelatinized maize starch, hydroxypropyl methylcellulose or polyvinylpyrrolidone); fillers (e.g., lactose, calcium hydrogen phosphate, or microcrystalline cellulose); lubricants (e.g., magnesium stearate, silica, or talc); disintegrants (e.g., potato starch or sodium starch glycolate); or wetting agents (e.g., sodium lauryl sulfate). Oral formulations may also contain sweetening, flavoring, coloring and preservative agents. Pharmaceutically acceptable excipients for tablet forms may comprise nontoxic ingredients such as inert diluents, such as calcium carbonate, sodium carbonate, lactose, calcium phosphate, or sodium phosphate, and the like. Tablets may be coated using methods well known in the art. Liquid preparations for oral administration may take the form of, for example, solutions, syrups or suspensions, or they may be presented as a dry product for reconstitution with water or other suitable vehicle before use. Such liquid preparations may be prepared by any conventional means with pharmaceutically acceptable additives such as suspending agents (e.g., sorbitol syrup cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). In some alternatives, the preparations may also contain buffer salts, flavoring, coloring and sweetening agents as appropriate.

In the case of tablets for oral use, carriers which are commonly used include lactose and corn starch, and lubricating agents such as magnesium stearate are commonly added. For oral administration in capsule form, useful carriers include lactose and corn starch. Further non-limiting examples of carriers and excipients include milk, sugar, certain types of clay, gelatin, stearic acid or salts thereof, calcium stearate, talc, vegetable fats or oils, gums and glycols.

Surfactants which can be used to form pharmaceutical compositions and dosage forms can include, but are not limited to, hydrophilic surfactants, lipophilic surfactants, and mixtures thereof. In some alternatives, a mixture of hydrophilic surfactants may be employed. In some alternatives, a mixture of lipophilic surfactants may be employed. In some alternatives, a mixture of at least one hydrophilic surfactant and at least one lipophilic surfactant may be employed.

In some alternatives, one or more preservatives or other materials can be provided to the formulations for enhancing the therapeutic, neutraceutical, pharmaceutical, or other properties of the composition.

Methods of Treatment

The term "treating" and its grammatical equivalents as used herein include achieving a therapeutic benefit and/or a prophylactic benefit. By therapeutic benefit is meant amelioration or eradication of the underlying disorder being treated. Also, a therapeutic benefit is achieved with the amelioration or eradication of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made. In some alternatives, the bioactive compositions can be administered to a subject to prevent progression of physiological symptoms or of the underlying disorder.

In some alternatives, the therapeutic agent is present in an amount sufficient to exert a therapeutic effect by an average of at least about 5, 10, 15, 20, 25, 30, 40, 50, 60, 70, 80, 90, more than 90%, or substantially eliminate the disease or at least one of its underlying symptoms. Preferably the therapeutic effect is an effect on an eye condition or a hair condition.

In some alternatives, the therapeutic agent is present in an amount sufficient to exert a therapeutic effect to reduce symptoms of a disease or a health condition, such as an eye condition or a hair condition, by an average of at least about 5, 10, 15, 20, 25, 30, 40, 50, 60, 70, 80, 90, more than 90%, or substantially eliminate symptoms of the eye condition or hair condition.

Eye Treatments

Administration: In order to reduce inflammation in eye disorders, the bioactive composition is preferably delivered to the ocular surface, interconnecting innervation, conjunctiva, lacrimal glands, or meibomian glands. It is envisioned that effective treatment can encompass administering therapeutic agents via oral administration, topical administration, via injection, intranasally, transdermally, via an impregnated or coated device such as an ocular insert or implant, or iontophoretically, among other routes of administration.

For administration via injection, the bioactive composition can be injected intramuscularly, intra-arterially, subcutaneously, or intravenously. A pump mechanism may be employed to administer the pharmaceutical composition over a preselected period. In some alternatives, it is desirable to deliver drug locally, thus injections may be made periocularly, intraocularly, subconjunctively, retrobulbarly, or intracamerally. In some alternatives, systemic delivery is preferred.

For systemic administration, the bioactive compositions can be formulated for and administered orally. For administration that may result in either regional or systemic distribution of the therapeutic agents, the composition of the invention may be administered intranasally, transdermally, or via some forms of oral administration such as, for example, with use of a mouthwash or lozenge incorporating a compound that is poorly absorbed from the gastrointestinal (G.I.). For administration that may result in regional or local delivery of the composition, iontophoretic or topical administration may be used.

Additionally, the bioactive compositions and formulations disclosed herein may be administered to the ocular surface via a pump-catheter system, or released from within a continuous or selective release device such as, e.g., membranes such as, but not limited to, those employed in the Ocusert® System (Alza Corp, Palo Alto, Calif.) and those described in Kuno et al. (Polymers 3:193-221, 2011). The pharmaceutical compositions can be incorporated within, carried by or attached to contact lenses which are then worn by the subject. The bioactive compositions and formulations can be sprayed onto ocular surface.

Intranasal administration may utilize an aerosol suspension of respirable particles comprising a bioactive composition or formulation disclosed herein, which the subject inhales. The compositions and formulations are absorbed into the bloodstream via pulmonary absorption or contact the lacrimal tissues via nasolacrimal ducts, and subsequently be delivered to the lacrimal tissues in a pharmaceutically effective amount. The respirable particles may be solid or liquid, with suitably sized particles, as is known in the art to be effective for absorption. Compositions and formulations for inhalation or insufflation can include solutions and suspensions in pharmaceutically acceptable, aqueous or organic solvents, or mixtures thereof, and powders. The liquid or solid compositions may contain suitable pharmaceutically acceptable excipients as described elsewhere herein. Preferably the compositions and formulations disclosed herein are administered by the oral or nasal respiratory route for local or systemic effect. In some alternatives, compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

For transdermal administration, any suitable formulation known in the art may be utilized, either as a solution, suspension, gel, powder, cream, oil, solids, dimethylsulfoxide (DMSO)-based solutions or liposomal formulation for use in a patch or other delivery system known in the art. The compositions and formulations also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, alcohols (e.g., ethanol), fatty acids (e.g., oleic acid), humectants (e.g., urea), glycols (e.g., propylene glycol), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols. The construction and use of transdermal patches for the delivery of pharmaceutical agents is well known in the art. Such patches may be constructed for continuous, pulsatile, or on demand delivery of pharmaceutical agents.

For topical administration, all the formulations for topical ocular administration used in the field of ophthalmology (e.g., eye drops, eye packs, impregnated contact lenses, inserts, pump delivery systems, dimethylsulfoxide (DMSO)-based solutions suspensions, liposomes, and eye ointment) and all the formulations for external use in the fields of dermatology and otolaryngology (e.g., ointment, cream, gel, lotion, crystalline forms, foam, powder, salve, and spray) may be utilized as is commonly known in the art. Additionally all suitable formulations for topical administration to skin and mucus membranes of the nasal passages may be utilized to deliver the present compositions and formulations. In some alternatives, the bioactive compositions and formulations may be a liposomal formulation for topical or oral administration, any of which are known in the art.

Lubricants which can be used to form pharmaceutical compositions and dosage forms include, but are not limited to, calcium stearate, light mineral oil, mannitol, magnesium stearate, mineral oil, glycerin, polyethylene glycol, sorbitol, other glycols, stearic acid, sodium lauryl sulfate, talc, hydrogenated vegetable oil (e.g., cottonseed oil, corn oil, olive oil, peanut oil, sunflower oil, sesame oil, and soybean oil), zinc stearate, ethyl oleate, ethyl laureate, agar, or mixtures thereof. Additional lubricants include, for example, a Syloid® silica gel, a coagulated aerosol of synthetic silica, or mixtures thereof. A lubricant can optionally be added, in an amount of less than about 1% w/w, preferably less than 0.5% w/w, most preferably less than 0.25% w/w of the pharmaceutical composition.

Additionally, it is envisioned that the compositions and formulations disclosed herein may be attached releasably to biocompatible polymers for use in sustained release formulations on, in or attached to inserts for topical or systemic administration. The controlled release from a biocompatible polymer may be utilized with a water soluble polymer to form an instillable formulation, as well.

Eye drops may be prepared by dissolving the active ingredient, i.e. a bioactive composition disclosed herein, in a sterile aqueous solution such as physiological saline, buffering solution, and the like, or by combining powder compositions to be dissolved before use. Other vehicles may be chosen, as is known in the art, including but not limited to, balance salt solution, saline solution, water soluble polyethers such as polyethylene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some alternatives, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., methyl cellulose, hydroxy propyl methylcellulose, hydroxyethyl cellulose, carboxymethyl cellulose, hydroxy propyl cellulose, sodium polyacrylate, carboxyvinyl polymer, crosslinked polyacrylate, polyvinyl alcohol, polyvinyl pyrrolidone, or other agents known to those skilled in the art).

The solubility of the components of the present compositions and formulations may be enhanced by a surfactant or other appropriate co-solvent in the composition. Such co-solvents can include polysorbate 20, polysorbate 60, polysorbate 80, Pluronic F68, Pluronic F-84, Pluronic P-103, cyclodextrin, or other agents known to those skilled in the art. In some alternatives, such co-solvents can be employed at a level of from about 0.01% to 2% by weight. In some alternatives, such co-solvents can be employed at a level of from about 0.5% to 1% by weight.

In some alternatives, the bioactive compositions disclosed herein can be formulated as a sterile unit dose type containing no preservatives. The compositions can be packaged in multi-dose form. Preservatives can be preferred to prevent microbial contamination during use. Suitable preservatives include: benzalkonium chloride, chlorobutanol, edetate disodium (EDTA), methyl paraben, Onamer M, propyl paraben, phenylethyl alcohol, sorbic acid, thimerosal, or other agents known to those skilled in the art. In some ophthalmic products according to come alternatives, such preservatives can be employed at a level of from 0.004% to 0.02%. In some alternatives, the preservative, preferably benzalkonium chloride, may be employed at a level of from 0.001% to less than 0.01%, e.g. from 0.001% to 0.008%, preferably about 0.005% by weight. In some alternatives, a concentration of benzalkonium chloride of 0.005% may be sufficient to preserve the compositions and formulations disclosed herein from microbial contamination.

The amount of administration and the number of administrations of the active ingredient used in the present compositions and methods vary according to sex, age and body weight of patient, symptoms to be treated, desirable therapeutic effects, administration routes and period of treatment. For eye drops for an adult, the formulations containing the active compositions disclosed herein may range in concentration from about 0.0001 to 10.0 W/V %, about 0.005 to 10.0 W/V %, about 0.01 to 10.0 W/V %, about 0.05 to 10.0 W/V %, about 0.1 to 10.0 W/V %, about 0.5 to 10.0 W/V %, about 1.0 to 10.0 W/V %, about 20 to 10.0 W/V %, about 3.0 to 10.0 W/V %, about 4.0 to 10.0 W/V %, or about 5.0 to 10.0 W/V %. One alternative has a formulation of about 1.0 to 10.0 W/V % of the active compositions disclosed herein. One alternative has a formulation of about 0.01 to 10.0 W/V % of the active compositions disclosed herein. One alternative has a formulation of about 5.0 to 10.0 W/V % of the active compositions disclosed herein. The administration may be administered several times a day per eye, preferably one to ten times, more preferably one to four times, most preferably once a day. The size of the drop administered may be in the range of about 10-100µl, about 10-90 µl, about 10-80 µl, about 10-70 µl, about 10-60 µl, about 10-50 µl, about 10-40 µl, about 10-30 µl, about 20-100 µl, about 20-90 µl, about 20-80 µl, about 20-70 µl, about 20-60 µl, about 20-50 µl, about 20-40 µl, or about 20-30 µl. One alternative administers a drop in the range of 10-30 µl. One alternative administers a drop in the range of 10-100 µl. One alternative administers a drop in the range of 20-50 µl. One alternative administers a drop in the range of 10-60 µl.

In some alternatives, the bioactive formulations disclosed herein may be administered several drops per time, one to four drops, preferably one to three drops, more preferably one to two drops, and most preferably one drop per day.

In formulations for ointment, cream, lotion or spray, the concentration of the active compositions in the formulations may range about 0.0001 to 10.0 W/V %, about 0.005 to 10.0 W/V %, about 0.01 to 10.0 W/V %, about 0.05 to 10.0 W/V %, about 0.1 to 10.0 W/V %, about 0.5 to 10.0 W/V %, about 1.0 to 10.0 W/V %, about 20 to 10.0 W/V %, about 3.0 to 10.0 W/V %, about 4.0 to 10.0 W/V %, or about 5.0 to 10.0 W/V %. One alternative has a formulation of about 1.0 to 10.0 W/V of the compounds of the invention. One alternative has a formulation of about 0.01 to 10.0 W/V % of the compounds of the invention. One alternative has a formulation of about 5.0 to 10.0 W/V % of the compounds of the invention. These formulations may be applied or sprayed several times a day, preferably one to six times, more preferably one to four times, and most preferably once a day. The compounding ratio of each ingredient may be suitably increased or decreased based on the degree of inflammations or infections.

The bioactive formulations can further include other pharmacological active ingredients as far as they do not contradict the purpose of the present invention. In a combination of plural active ingredients, their respective contents may be suitably increased or decreased in consideration of their effects and safety.

Treating Hair Conditions

Hair is a complex, multi-layered and dynamic system that provides a protective covering from elements and acts to disperse products from glands in acting as an interactive boundary between an organism and the environment. Often, it is also vitally important to both individual health and self-image. For example, a significantly large industry has developed to assist individuals with conditions of hair loss (alopecia) as well as to deal with excessive hair growth. In fact, a large array of hair conditions and disorders have been characterized and include alopecia, androgenic alopecia, alopecia greata, permanent alopecia, anagen growth state disorders, anagen effluvium, bulb disorders, bulge disorders, catagen and regression disorders, club hair, hirsutism, hypertrichosis, lanugo hair, miniaturization, telogen disorders, telogen effluvium, terminal hair, and vellus hair as non-limiting examples.

The bioactive composition, in some alternatives, can include culture media that have been conditioned by using two or more cell lines. Preferably, at least one of the cell lines used is hair dermal papilla cells. Hair papilla cells are a type of mesenchymal stem cell that plays a pivotal role in hair formation, growth and restoration. In some alternatives, the conditioned culture media can be preferably concentrated and applied as a topical formulation. In some alternatives, the bioactive compositions disclosed herein can be formulated for topical applications using an agent that facilitates penetration of the compound into the skin, for example, DMSO, and applied as a topical application for stimulating hair growth.

Some alternatives disclosed herein relate to a method of treating a hair condition. In some particular alternatives, the method includes administering to the subject a therapeutically effective amount of a bioactive formulation disclosed herein, thereby stimulating hair growth. In some alternatives, the hair condition to be treated is selected from the group consisting of pattern baldness, alopecia caused by chemotherapy, hair thinning due to aging, illness, stress, traction alopecia, and genetic disorders. In some alternatives, the subject exhibits an improved stimulation of hair growth at a body area, such as at the scalp, back, beard, eyebrows, lashes, leg, arm, pubic region, or a combination of any thereof. In some alternatives, the hair growth is due to thickened hair sheath diameter, increased hair diameter, increased rate of growth in hair length, increased thickness, differentiation of quiescent hair follicles into more mature forms, the appearance of proliferation of new hair follicle, or a combination of any thereof. In some alternatives of this and other aspects of the disclosure, bioactive formulation is administered topically. In some alternatives, bioactive formulation is administered transdermally. In some alternatives, bioactive formulation is administered in a suitable form, such as in the form of a lotion, a gel, an ointment, a cream, a powder, a salve, a foam, a spray, an exosome, or a liposome.

In some alternatives, the bioactive compositions disclosed herein promote or restore hair growth when applied topically by providing growth factors and other factors that increase epithelial cell migration to hair follicles. In addition to the growth factors found in the conditioned culture media, other compounds, such as minoxidil and antibiotics can be used. Since it has been previously reported that there is a reduction in blood supply during catagen (the transitional phase of the hair follicle between growth and resting phases) and telogen (the resting phase), biologically active molecules derived from the conditioned cell medium can be determined and optimized for use during these phases using assays known in the art including the stump-tailed macaque model for male-patterned baldness. See, for example, Rittmaster R S et al., J. Clin. Endocrinol. Metab., 65(1):188-93, 1987; Brigham P A et al., Clin. Dermatol., 6(4):177-87, 1988; Holland, J M, Clin. Dermatol., 6(4):159-162, 1988; Pan H J et al., Endocrine, 9(1):39-43, 1988, and Diani A R et al., J. Invest. Dermatol., 102(4): p. 511-4, 1994. Additional models include measuring differences in hair follicle proliferation from follicles cultured from bald and hairy areas, a newborn rat model as well as a rat model of alopecia areata. See, McElwee K J et al., Br. J. Dermatol., 135(2):211-7, 1996; Michie H J. et al., Br. J. Dermatol., 123(5):557-67, 1990; Hussein A M, Int. J. Dermatol., 34(7):470-3, 1995; Neste D V, Dermatol Clin., 14(4):609-17, 1996; Oliver R F et al., J. Invest. Dermatol., 96(5):978, 1991.

Kits

Some alternatives disclosed herein relate to kits. The kits, in some alternatives, include an active composition or formulation disclosed herein in suitable packaging, and written material that can include instructions for use, discussion of clinical studies, listing of side effects, and the like. The kit can further contain another therapeutic agent that is co-administered with the bioactive compositions and formulations disclosed herein. In some alternatives, the therapeutic agent and the bioactive compositions and formulations disclosed herein are provided as separate compositions in separate containers within the kit. In some alternatives, the therapeutic agent and the bioactive compositions and formulations disclosed herein are provided as a single composition within a container in the kit. Suitable packaging and additional articles for use (e.g., measuring cup for liquid preparations, foil wrapping to minimize exposure to air, dispensers, and the like) are known in the art and may be included in the kit.

Throughout this disclosure, various information sources are referred to and incorporated by reference. The information sources include, for example, scientific journal articles, patent documents, textbooks, and World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use the alternatives disclosed herein, any discussion and comment in a specific information source should no way be considered as an admission that such comment was widely accepted as the general opinion in the field.

The bioactive compositions and formulations disclosed herein can be used to promote or restore hair growth when applied topically by providing growth factors and other factors that increase epithelial cell migration to hair follicles. In addition to the growth factors generally present in the conditioned culture media, other compounds, such as minoxidil (in, e.g., topical applications), finasteride (in, e.g., oral applications), and antibiotics can be included in the bioactive compositions and formulations. It has been previously reported that there is a reduction in blood supply during catagen (the transitional phase of the hair follicle between growth and resting phases) and telogen (the resting phase). Biologically active molecules, e.g. "stem cell released molecules" or SRM's, derived from the conditioned culture media disclosed herein can be determined and optimized for use during these phases using assays known in the art including the stump-tailed macaque model for male-patterned baldness. Additional models include measuring differences in hair follicle proliferation from follicles cultured from bald and hairy areas, a newborn rat model as well as a rat model of alopecia areata.

The discussion of the general methods given herein is intended for illustrative purposes only. Other alternative methods and alternatives will be apparent to those of skill in the art upon review of this disclosure, and are to be included within the spirit and purview of this application.

It should also be understood that the following examples are offered to illustrate, but not limit, the invention.

EXAMPLES

Example 1

Active Composition for Treatment of Ocular Surface Disease

In one example, a therapeutic composition for treatment of ocular surface disease included about 50% v/v conditioned medium derived from cell culture of a Human Adipose Derived Stem Cell (ADSC) line and about 50% v/v conditioned medium derived from cell culture of a Human Dermal Fibroblasts (HDF-f).

Cultivation of Human Adipose Derived Stem Cells (hADSC)

Preparation of MesenPro RS™ Medium

Growth media used in this experiment is Complete MesenPRO RS™ Medium which is a reduced serum (2%) medium specifically formulated to support the growth of human mesenchymal stem cells (hMSCs) in culture. Typically, when growing in MesenPRO RS™ Medium, hMSCs can be expanded for multiple passages while maintaining their multipotential characteristics (i.e., differentiation into osteogenic, chondrogenic, and adipogenic lineages).

The Complete MesenPRO RS™ medium was prepared prior to use as follows. 10 mL of frozen MesenPRO RS™ GrowthSupplement (Catalog No. 12748) was slowly thawed at 37° C. and aseptically added to 500 mL of MesenPRO RS™ Basal Medium (Catalog No. 12747). The resultant solution was mixed thoroughly prior to the addition of 5 mL of a 100× L-glutamine stock solution (Glutamax, 200 mM L-glutamine; Catalog No. 35050). After preparation, the Complete MesenPRO RS™ medium was stored in the dark at 4° C. and used within 15 days.

Establishment of hADSC Cultures

Cells of STEMPRO® Human Adipose-Derived Stem Cells (hADSCs) (Life Technologies, Carlsbad) in a commercial frozen vial were thawed quickly by swirling the vial in a 37° C. water bath (1-2 minutes). Once thawed, hADSCs were immediately transferred into a 50-mL sterile conical tube containing 10-mL of pre-warmed Complete MesenPRO RS™ medium with gentle mixing at 37° C. Cell suspension was centrifuged for 150×g at room temperature. The supernatant was discarded and the conical tube was drained briefly over sterile gauze. Cell pellet was loosen by lightly tapping the tube on a hard surface, and gently resuspended in 10 mL of pre-warmed Complete MesenPRO RS™ medium (37° C.). 75 µL of the hADSC cell suspension was mixed with 75 µL of 0.4% Trypan Blue solution, and a cell count was determined by using a hemacytometer.

Seeding

The hADSC cell culture established as described above was aseptically seeded into a T75 flask (Sigma, Cat. No. Z707546) or a HYPERFlask® Cell Culture Vessel. For T75 flasks, 25-26 mL Complete MesenPRO RS™ media was pre-warmed to 37° C. prior to being seeded with approximately $5 \times 10^3$ cells per $cm^2$, i.e. $3.75 \times 10^5$ cells per flask. T75 flasks were then gently rocked to disperse the seeded cells evenly over the growth surface.

For Corning HYPERFlask® vessels, Complete MesenPRO RS™ media was pre-warmed to 37° C. prior to being seeded with approximately $4 \times 10^6$ cells per flask. This seeding density typically supports the cell culture in the HYPERFlask™ vessel reaching a cell density of 90-95% within 7-8 days. For this purpose, an appropriate volume of cell suspension was added to 500 mL of pre-warmed Complete MesenPRO RS™ media (37° C.), followed by the addition an appropriate volume of the growth medium to bring the total volume to 550 mL. The seeded growth medium was gently mixed by swirling, and transferred into a HYPERFlask™ vessel. If occurred, excessive bubbles were removed and, if needed, additional growth medium was added to bring the fluid level in the flask equal to the second thread on the neck.

The following information of the cell culture was recorded: (1) live cell count; (2) viability; (3) total number of cells; (4) number of cells per flask; (5) volume of cell suspension added to each flask; and (6) the number and type of flasks seeded. After seeding, T75 flasks were placed on stainless steel tray in a humidified growth chamber, and incubated at 37° C. and in the presence of 5% $CO_2$. HYPERFlask™ vessels are incubated directly on the incubator shelf.

Harvest Conditioned Culture Medium, Passage and Freeze Cells from HYPERFlask™ vessels Harvest SRM-containing Conditioned Media Upon reaching about 90-98% confluence, the cell cultured medium was aseptically transferred to a filter unit equipped with a 0.2 µM PES (polyethlysulfone) sterile filtration device. For this purpose, the HYPERFlask™ vessel was slowly tilted to pour the conditioned cell cultured medium, which was determined to contain SRMs, into the filter unit. While pouring, the flask was slowly rotated 180° until the cell cultured medium was flowing down the angle neck (air dam) of the flask. When necessary, the flask was gently rocked back and forth while inverted to drain any remaining liquid. The SRM-containing conditioned culture medium was filtered and subsequently stored in sterile polycarbonate bottles at –30° C.

Passage Cells from HYPERFlask™ Vessel

After cell cultured medium was removed, 100 mL of rinsing solution (DPBS, Dulbecco's Phosphate Buffered Saline; Invitrogen Cat. No. 14190) was added to the HYPERFlask™ vessel. The flask was recapped and lay on its side to allow the rinsing solution to distribute evenly between layers. The flask was then rotated back and forth 180° along its long axis several times (at least 4 times) so that the entire cell sheet in each layer is thoroughly rinsed. The flask was turned over and the rotation was repeated. The rinsing solution was discarded, and replaced by 50 mL of dissociation solution (TRYPLE Expression, Invitrogen). The flask was recapped and lay on its side to allow the rinsing solution to distribute evenly between layers. The flask was then rotated back and forth 180° along its long axis several times (at least 4 times) so that the entire cell sheet in each layer is thoroughly coated. The flask was turned over and the rotation was repeated to facilitate cell detachment. Microscopy was used to visually monitor cell detachment, which typically took less than 5 minutes. Once most cells were rounded and dislodged, the flask was shaken sharply and repeatedly to dislodge remaining cells.

Two 25-mL aliquots of 25 mL dislodged cells from each HYPERFlask™ vessel were transferred into two 50 mL conical centrifuge tubes each containing 20 mL of Complete MesenPRO RS™ medium pre-warmed at 37° C. The tubes were centrifuged at 200-210×g for 5 minutes at room temperature. After supernatant was discarded, the cell pellets was gently resuspended in 10-12 mL of Complete MesenPRO RS™ medium pre-warmed at 37° C., and were pooled into a single tube. 75 µL of the pooled cell suspension was mixed with 75 µL of 0.4% Trypan Blue solution, and a cell count was determined by using a hemacytometer before the cell suspension was used to seed additional HYPERFlask™ vessels.

The seeding densities were as follows.
a. Passage 4-5: $4.0$-$4.1 \times 10^6$ cells per flask.
b. Passage 6-7: $4.2$-$4.3 \times 10^6$ cells per flask.
c. Passage 8-10: $4.4$-$4.5 \times 10^6$ cells per flask.

For each of the flasks, a container was prepared with an appropriate volume of cell suspension combined with 500 mL of pre-warmed Complete MesenPRO RS™ media (37° C.), followed by the addition an appropriate volume of the growth medium to bring the total volume to 550 mL. The seeded growth medium was gently mixed by swirling to avoid generating foam, and transferred into a HYPERFlask™ vessel. If occurred, excessive bubbles were removed either by using a sterile transfer pipet or a serological pipet, or by tilting the flask from side to side firmly to dislodge bubbles trapped in the flask. If needed, additional growth medium was added to bring the fluid level in the flask equal to the second thread on the neck. The flasks were then recapped and incubated in a humidified growth chamber, at 37° C. and in the presence of 5% $CO_2$.

General Protocol for Preparing Frozen Stocks of hADSC Cells

Partial or entire contents of HYPERFlask™ vessels are used for the preparation of frozen cell stocks by using a procedure similar to the passage protocol described above, through the centrifugation step. After centrifugation, the cell pellets were suspended in an appropriate volume of freshly prepared freezing medium [70% Complete MesenPro RS™ Medium; 20% fetal bovine serum (FBS; ScienCell Res. Lab., Cat. No. 0500); and 10% dimethyl sulfoxide (DMSO, Sigma Aldrich, Cat. No. D-2650)]. Cell suspension was aliquoted in 1 mL cryovials. The number of ADSC cells per vial was preferably ranging from $4$-$8 \times 10^6$ cells. The cryovials were placed in freezing cans containing isopropanol (Thermo Scientific, Cat. No. 5100-0001). The freezing cans were placed in –85° C. overnight before being transferred to a vapor phase of a self-filling liquid nitrogen freezer.

Cultivation of Human Dermal Fibroblasts (HDF)

Preparation of Fibroblast Medium

Fibroblast medium (ScienCell Research Laboratories, Carlsbad, Calif., Cat. No. 2301) was prepared according to the manufacturer instructions, with some modifications. 10 mL of frozen fetal bovine serum (Cat. No. 0010) and 5 mL of frozen of fibroblast growth factor (Cat. No. 2352) were thoroughly thawed and mixed at 37° C. before they were added to each 500 mL of fibroblast medium (Cat. No. 2301). Once prepared, the complete fibroblast medium was subsequently stored in the dark at 4° C. and used within 15 days.

Establishment of HDF Cultures

Cells of Human Dermal Fibroblasts in a commercial frozen vial were thawed quickly by swirling the vial in a 37° C. water bath (1-2 minutes). Once thawed, HDFs were immediately transferred into a 50-mL sterile conical tube containing 10-mL of pre-warmed fibroblast medium at 37° C. with gentle mixing. Cell suspension was centrifuged for 200×g at room temperature. The supernatant was discarded and the conical tube was drained briefly over sterile gauze. The supernatant was discarded and the conical tube was drained briefly over sterile gauze. Cell pellet was loosen by lightly tapping the tube on a hard surface, and gently resuspended in 10 mL of pre-warmed fibroblast medium (37° C.). 75 μL of the HDF cell suspension was mixed with 75 μL of 0.4% Trypan Blue solution, and a cell count was determined by using a hemacytometer.

Seeding

The fibroblast cell culture established as described above was used to aseptically seed T75 flasks or HYPERFlask® Cell Culture Vessels. For T75 flasks, 25-26 mL fibroblast media was pre-warmed to 37° C. prior to being seeded with approximately $5 \times 10^3$ cells per $cm^2$, i.e. $3.75 \times 10^5$ cells per flask. For Corning HYPERFlask® vessels, fibroblast media was pre-warmed to 37° C. prior to being seeded with approximately $2-2.2 \times 10^6$ cells per flask. This seeding density typically supports the cell culture in the HYPERFlask™ vessel reaching a cell density of 90-95% within 7-8 days. For this purpose, an appropriate volume of cell suspension was added to 500 mL of pre-warmed fibroblast media (37° C.), followed by the addition an appropriate volume of the growth medium to bring the total volume to 550 mL. The seeded growth medium was gently mixed by swirling, and transferred into a HYPERFlask™ vessel. If occurred, excessive bubbles were removed and, if needed, additional growth medium was added to bring the fluid level in the flask equal to the second thread on the neck. After seeding, T75 flasks were placed on stainless steel tray in a humidified growth chamber, and incubated at 37° C. and in the presence of 5% $CO_2$. Whenever available, a tri-gas incubator with hypoxic conditions (5% $O_2$) was used. HYPERFlask™ vessels are incubated directly on the incubator shelf.

Harvest SRM, Passage and Freeze Cells from HYPERFlask™ Vessels

Harvest SRM-containing Conditioned Media

Upon reaching about 90-98% confluence, the cell cultured medium was aseptically transferred to a filter unit equipped with a 0.2 μM PES (polyethlysulfone) sterile filtration device. For this purpose, the HYPERFlask™ vessel was slowly tilted to pour the conditioned culture medium, which was determined to contain SRMs, into the filter unit. While pouring, the flask was slowly rotated 180° until the cell cultured medium was flowing down the angle neck (air dam) of the flask. When necessary, the flask was gently rocked back and forth while inverted to drain any remaining liquid. The SRM-containing cultured medium was filtered and subsequently stored in sterile polycarbonate bottles at −30° C.

Passage Cells from HYPERFlask™ Vessel

After cell cultured medium was removed, 100 mL of rinsing solution (DPBS, Dulbecco's Phosphate Buffered Saline; Invitrogen Cat. No. 14190) was added to the HYPERFlask™ vessel. The flask was recapped and lay on its side to allow the rinsing solution to distribute evenly between layers. The flask was then rotated back and forth 180° along its long axis several times (at least 4 times) so that the entire cell sheet in each layer is thoroughly rinsed. The flask was turned over and the rotation was repeated. The rinsing solution was discarded, and replaced by 50 mL of dissociation solution, which contained 10 mL Trypsin-EDTA (ScienCell, Cat. No. 0103) and 40 mL DPBS. The flask was recapped and lay on its side to allow the rinsing solution to distribute evenly between layers. The flask was then rotated back and forth 180° along its long axis several times (at least 4 times) so that the entire cell sheet in each layer is thoroughly coated. The flask was turned over and the rotation was repeated to facilitate cell detachment. Microscopy was used to visually monitor cell detachment, which typically took less than 5 minutes. Once most cells were rounded and dislodged, the flask was shaken sharply and repeatedly to dislodge remaining cells.

Two 25-mL aliquots of 25 mL dislodged cells from each HYPERFlask™ vessel were transferred into two 50 mL conical centrifuge tubes each containing 10 mL of fetal bovine serum (FBS, ScienCell, Cat. No. 0500). The tubes were centrifuged at 200-210×g for 5 minutes at room temperature. After supernatant was discarded, the cell pellets were gently resuspended in 10-12 mL of complete firboblast medium pre-warmed at 37° C., and were pooled into a single tube. 75 μL of the pooled cell suspension was mixed with 75 μL of 0.4% Trypan Blue solution, and a cell count was determined by using a hemacytometer before the cell suspension was used to seed additional HYPERFlask™ vessels.

The seeding densities were as follows.
a. Passage 4-5: $2.0-2.1 \times 10^6$ cells per flask.
b. Passage 6-7: $2.2-2.3 \times 10^6$ cells per flask.
c. Passage 8-10: $2.4-2.5 \times 10^6$ cells per flask.

For each of the flasks, a container was prepared with an appropriate volume of cell suspension combined with 500 mL of pre-warmed fibroblast media (37° C.), followed by the addition an appropriate volume of the growth medium to bring the total volume to 550 mL. The seeded fibroblast medium was gently mixed by swirling to avoid generating foam, and transferred into a HYPERFlask™ vessel. If occurred, excessive bubbles were removed either by using a sterile transfer pipet or a serological pipet, or by tilting the flask from side to side firmly to dislodge bubbles trapped in the flask. If needed, additional growth medium was added to bring the fluid level in the flask equal to the second thread on the neck. The T75 flasks were then recapped and incubated in a humidified growth chamber, at 37° C. and in the presence of 5% $CO_2$. Whenever available, a tri-gas incubator with hypoxic conditions (5% $O_2$) was used. The HYPERFlask™ vessels were incubated directly on the incubator.

General Protocol for Preparing Frozen Stocks of HDF Cells

Partial or entire contents of HYPERFlask™ vessels are used for the preparation of frozen cell stocks by using a procedure similar to the passage protocol described above, through the centrifugation step. After centrifugation, the cell pellets were suspended in an appropriate volume of freshly prepared HDF freezing medium [80% complete fibroblast medium; 10% fetal bovine serum (FBS; ScienCell Res. Lab., Cat. No. 0500); and 10% dimethyl sulfoxide (DMSO, Sigma Aldrich, Cat. No. D-2650)]. Cell suspension was aliquoted in 1 mL cryovials. The number of HDF cells per vial preferably ranged from $4-6 \times 10^6$ cells. The cryovials were placed in freezing cans containing isopropanol (Thermo Scientific, Cat. No. 5100-0001). The freezing cans were placed in −85° C. overnight before being transferred to a vapor phase of a self-filling liquid nitrogen freezer.

In accordance with some alternatives of the invention, an amount of ADSC and an amount of HDF-f cell lines were individually provided in nutrient media and thawed in a water bath prior to sub culturing (passaging) in flasks. Upon reaching about 90% confluence, the respective conditioned media containing SRM's were harvested. Here, a sterile pipette was used to remove medium containing the ADSC and SRM-containing conditioned media from flasks and transferred to a 500 mL filter unit having a 0.33 μM pore size. Upon transfer of the medium, vacuum was applied and the SRM's were filtered into a receptacle. The SRM-containing conditioned media were then aliquoted and stored in sterile containers for subsequent use.

Subsequent to removing SRM-containing conditioned media, the cells were passaged and frozen. Dulbecco's phosphate buffered saline (DPBS) was used to lift cells from the surface of flasks and MesenPro RS medium was used for culture.

The HDF-f cells were similarly processed to extract SRM-containing conditioned media, passage cells, and freeze. HDF-f cells were cultured in fibroblast medium.

The SRM-containing conditioned media derived from ADSC cultures and HDF-f cultures were each thawed in a water bath at 37° C. and combined in a 50/50 ratio by volume. The conditioned media were then filtered by vacuum into an all-in-one receptacle and stored in a sterile container at 4° C.

Example 2

Composition for Hair Growth Treatment

In another example, a hair growth treatment product is produced in accordance with some alternatives of the present disclosure. In this example, the first cell line was StemPro® Human Adipose-Derived Stem (Life Technologies, Carlsbad, Cat. No. R7788115), the second cell line was HUMAN HAIR DERMAL PAPILLA CELLS (HHDPC; ScienCell Research Laboratories, Cat. No. 2400), and the third cell line was Human Dermal Fibroblasts-fetal (HDF-f) (ScienCell Research Laboratories, Cat. No. 2300)

Cultivation of Human Hair Dermal Papilla Cells (HHDPC)
Preparation of Mesenchymal Stem Cell Medium Mesenchymal Stem Cell Medium (MSMC, ScienCell Research Laboratories, Carlsbad, Calif., Cat. No. 2301) was prepared according to the manufacturer instructions, with some minor modifications. 25 mL of frozen of fetal bovine serum (Cat. No. 0025) and 5 mL 100× of frozen Mesenchymal Stem Cell Growth Supplement (Cat. No. 7552) were thoroughly thawed and mixed at 37° C. before they were added to each 500 mL of Mesenchymal Stem Cell Medium (Cat. No. 7501). Once prepared, the MSCM complete medium was subsequently stored in the dark at 4° C. and used within 15 days.

Establishment of HHDPC Cultures

Human Hair Dermal Papilla Cells in a commercial frozen vial were thawed quickly by swirling the vial in a 37° C. water bath (1-2 minutes). Once thawed, HHDPC cells were immediately transferred into a 50-mL sterile conical tube containing 10-mL of pre-warmed MSMC complete medium at 37° C. with gentle mixing. Cell suspension was centrifuged for 210×g at room temperature. The supernatant was discarded and the conical tube was drained briefly over sterile gauze. The supernatant was discarded and the conical tube was drained briefly over sterile gauze. Cell pellet was loosen by lightly tapping the tube on a hard surface, and gently resuspended in 10 mL of pre-warmed fibroblast medium (37° C.). 75 μL of the HHDPC cell suspension was mixed with 75 μL of 0.4% Trypan Blue solution, and a cell count was determined by using a hemacytometer.

Seeding

The HHDPC cell culture established as described above was used to aseptically seed T75 flasks or HYPERFlask® Cell Culture Vessels. For T75 flasks, 25-26 mL MSMC media was pre-warmed to 37° C. prior to being seeded with approximately $5 \times 10^3$ cells per $cm^2$, i.e. $3.75 \times 10^5$ cells per flask. The flasks were gently rocked to disperse cells evenly over growth surface. For Corning HYPERFlask® vessels, MSMC media was pre-warmed to 37° C. prior to being seeded with approximately $5 \times 10^6$ cells per flask. This seeding density typically supports the cell culture in the HYPERFlask™ vessel reaching a cell density of 90-95% within 7-8 days. For this purpose, an appropriate volume of cell suspension was added to 500 mL of pre-warmed MSMC media (37° C.), followed by the addition an appropriate volume of the growth medium to bring the total volume to 550 mL. The seeded growth medium was gently mixed by swirling, and transferred into a HYPERFlask™ vessel. If occurred, excessive bubbles were removed and, if needed, additional growth medium was added to bring the fluid level in the flask equal to the second thread on the neck. The following information of the cell culture was recorded: (1) live cell count; (2) viability; (3) total number of cells; (4) number of cells per flask; (5) volume of cell suspension added to each flask; and (6) the number and type of flasks seeded. After seeding, T75 flasks were placed in a humidified growth chamber, and incubated at 37° C. and in the presence of 5% $CO_2$. Whenever available, tri-gas incubator with hypoxic conditions (5% $O_2$) was used. HYPERFlask™ vessels are incubated directly on the incubator shelf.

Harvest SRM, Passage and Freeze Cells from HYPERFlask™ Vessels

Harvest SRM-containing Conditioned Media

Upon reaching about 90-98% confluence, the cell cultured medium was aseptically transferred to a filter unit equipped with a 0.2 μM PES (polyethlysulfone) sterile filtration device. For this purpose, the HYPERFlask™ vessel was slowly tilted to pour the conditioned culture medium, which was determined to contain SRMs, into the filter unit. While pouring, the flask was slowly rotated 180° until the cell cultured medium was flowing down the angle neck (air dam) of the flask. When necessary, the flask was gently rocked back and forth while inverted to drain any remaining liquid. The SRM-containing cultured medium was filtered and subsequently stored in sterile polycarbonate bottles at −30° C.

Passage HHDPC Cells from HYPERFlask™ Vessel

After cell cultured medium was removed, 100 mL of rinsing solution (DPBS, Dulbecco's Phosphate Buffered Saline; Invitrogen Cat. No. 14190) was added to the HYPERFlask™ vessel. The flask was recapped and lay on its side to allow the rinsing solution to distribute evenly between layers. The flask was then rotated back and forth 180° along its long axis several times (at least 4 times) so that the entire cell sheet in each layer is thoroughly rinsed. The flask was turned over and the rotation was repeated. The rinsing solution was discarded, and replaced by 50 mL of dissociation solution, which contained 10 mL Trypsin-EDTA (ScienCell, Cat. No. 0103) and 40 mL DPBS. The flask was recapped and lay on its side to allow the rinsing solution to distribute evenly between layers. The flask was then rotated back and forth 180° along its long axis several times (at least 4 times) so that the entire cell sheet in each layer is thoroughly coated. The flask was turned over and the rotation was repeated to facilitate cell detachment. Microscopy was used to visually monitor cell detachment, which typically took less than 5 minutes. Once most cells were rounded and dislodged, the flask was shaken sharply and repeatedly to dislodge remaining cells.

Two 25-mL aliquots of 25 mL dislodged cells from each HYPERFlask™ vessel were transferred into two 50 mL conical centrifuge tubes each containing 10 mL of fetal bovine serum (FBS, ScienCell, Cat. No. 0500). The tubes were centrifuged at 200-210×g for 5 minutes at room temperature. After supernatant was discarded, the cell pellets were gently resuspended in 10-12 mL of complete MSC medium pre-warmed at 37° C., and were pooled into a single tube. 75 µL of the pooled cell suspension was mixed with 75 µL of 0.4% Trypan Blue solution, and a cell count was determined by using a hemacytometer before the cell suspension was used to seed additional HYPERFlask™ vessels.

The seeding densities were as follows.

a. Passage 4-5: $5.0$-$5.1 \times 10^6$ cells per flask.
b. Passage 6-7: $5.2$-$5.3 \times 10^6$ cells per flask.
c. Passage 8-10: $5.5$-$5.6 \times 10^6$ cells per flask.

For each of the flasks, a container was prepared with an appropriate volume of cell suspension combined with 500 mL of pre-warmed MSC media (37° C.), followed by the addition an appropriate volume of the growth medium to bring the total volume to 550 mL. The seeded fibroblast medium was gently mixed by swirling to avoid generating foam, and transferred into a HYPERFlask™ vessel. If occurred, excessive bubbles were removed either by using a sterile transfer pipet or a serological pipet, or by tilting the flask from side to side firmly to dislodge bubbles trapped in the flask. If needed, additional growth medium was added to bring the fluid level in the flask equal to the second thread on the neck. The T75 flasks were then recapped and incubated in a humidified growth chamber, at 37° C. and in the presence of 5% $CO_2$. Whenever available, a tri-gas incubator with hypoxic conditions (5% $O_2$) was used. The HYPERFlask™ vessels were incubated directly on the incubator.

General Protocol for Preparing Frozen Stocks of HHDPC Cells

Partial or entire contents of HYPERFlask™ vessels are used for the preparation of frozen cell stocks by using a procedure similar to the passage protocol described above, through the centrifugation step. After centrifugation, the cell pellets were suspended in an appropriate volume of freshly prepared MSC freezing medium [80% complete fibroblast medium; 10% fetal bovine serum (FBS; ScienCell Res. Lab., Cat. No. 0500); and 10% dimethyl sulfoxide (DMSO, Sigma Aldrich, Cat. No. D-2650)]. Cell suspension was aliquoted in 1 mL cryovials. The number of HHDPC cells per vial preferably ranged from $4$-$6 \times 10^6$ cells. The cryovials were placed in freezing cans containing isopropanol (Thermo Scientific, Cat. No. 5100-0001). The freezing cans were placed in −85° C. overnight before being transferred to a vapor phase of a self-filling liquid nitrogen freezer.

Example 3

Preparation of S²RM (50% ADSC Conditioned Medium and 50% HDF-f Conditioned Medium)

Desired volumes of the conditioned culture medium derived from each of the cultured cell lines were thawed in 37° C. water bath. Equivalent volume of conditioned culture medium derived from each of the cultured cell lines was measured and deposited into the top compartment of an all-in-one filter unit that was equipped with polyethylsulfone membrane having 0.22 µM pore size. Vacuum was applied and the filtered conditioned culture medium was collected in the all-in-one receptacle. The top compartment of the all-in-one receptacle was removed and replaced with a sterile cap. The receptacle was then sealed with parafilm and stored at 4° C.

Example 4

Preparation of a Bioactive Composition that Contained HHDPC Conditioned Culture Medium Desired volumes of the conditioned culture medium derived from each of the cultured HHDPC cell lines were thawed in 37° C. water bath. Equivalent volumes of each conditioned culture medium derived from each of the cultured cell lines was measured and deposited into the top compartment of an all-in-one filter unit that was equipped with polyethylsulfone membrane having 0.22 µM pore size. Vacuum was applied and the filtered conditioned culture medium was collected in the all-in-one receptacle. The top compartment of the all-in-one receptacle was removed and replaced with a sterile cap. The receptacle was then sealed with parafilm and stored at 4° C.

In accordance with some alternatives, an amount of ADSC, HHDPC, and an amount of HDF-f cell lines were individually provided in nutrient media and thawed in a 37° C. water bath prior to sub culturing (passaging) in flasks. Upon reaching about 90% confluence, the respective conditioned culture media were harvested. A sterile pipette was used to remove medium containing the ADSC and conditioned culture media from flasks and transferred to a 500 mL filter unit having a 0.33 µM pore size. Upon transfer of the medium, vacuum was applied and the conditioned culture media were filtered into a receptacle. The conditioned culture media were then aliquoted and stored in sterile containers for subsequent use.

Subsequent to removing conditioned culture media from the ADSC medium, the cultured cells were passaged and frozen. Dulbecco's phosphate buffered saline (DPBS) was used to lift cells from the surface of flasks and MesenPro RS medium (Cat. No. 12746012, Life Technologies, Carlsbad, Calif) was used for culture.

The HDF-f cells and HHDPC cells were similarly processed to extract the respective SRM-containing conditioned media, passage cells, and freeze. HDF-f cells were cultured in fibroblast medium Fibroblast Medium (FM, Cat. No. 2301, ScienCell Res. Labs) and HHDPC cells were cultured in Mesenchymal Stem Cell Medium (MSCM, Cat. No. 7501, ScienCell Res. Labs).

The conditioned media that have been conditioned by ADSC, HHDPC, and HDF-f, respectively, were thawed in a water bath at 37° C. and combined in a 33/33/33 ratio by volume. The combined condition media were filtered by vacuum into an all-in-one receptacle and stored in a sterile container at 4° C.

In accordance with the above alternative, fibroblasts have been shown to release a SRM that includes the following molecules: Osteonectin, decorin, collagens I,III,IV, V, fibronectin, fibrillin, laminins, and hyaluronic acid. Each of these molecules can be harvested and incorporated into the composition for hair growth treatment.

In accordance with the above alternative, mesenchymal stem cells have been shown to release molecules that include: HLA-A, -B, and -C, exosomes, MSC IL-6, M-CSF, PGE2, IDO, TGF-, HLA-G, and PGE2, IL-I, IL-6, GDNF, BDNF, IGF-I, VEGF, GDNF, NGF, bFGF, BMP-4, bFGF, VEGF, PDGF, IL-I p, IL-I O, stem cell-derived factor-(SDF-)I, HGF, IGF-I, thymosin-P4, and Wnt5a, IL-I P and TNF-a, bFGF, HGF, angiopoietin-I and -2 (Ang-I and -2), cysteine-rich protein 6 I, antioxidants, proteasomes. Each of these molecules can be harvested and incorporated into the composition for hair growth treatment.

In accordance with above alternative, HUMAN HAIR DERMAL PAPILLA CELLS (hHDP) have been shown to release molecules that include: Wnt and Bmp, SOX2, β-catenin. The (hHDP) cells must be cultured only through early passage because in the state of early passage the hHDP produce only positive hair growth factors, whereas in later passages, the state of the hHDP produces and releases molecules, such as interferon β, that are negative regulators of hair growth. Each of these molecules can be harvested and incorporated into the composition for hair growth treatment.

While particular alternatives of the present invention have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A method for treating an eye condition in a subject in need thereof, comprising administering to said subject a therapeutically effective amount of a bioactive formulation that comprises a composition prepared by
   culturing cells of a first cell line and a second cell line in a first and a second culture medium, wherein said cultured cells secrete extracellular products into said culture medium so that a first conditioned culture medium and a second conditioned culture medium are formed;
   separating said first and second conditioned culture media from respective said cultured cells; and
   combining said first and said second conditioned culture media to form the composition,
   wherein said first and second cell lines are an adult human adipose derived stem cell (ADSC) line and a fetal human fibroblast cell line.

2. The method of claim 1, wherein said administering comprises topical administration of said bioactive formulation to an eye of said subject via a carrier vehicle selected from the group consisting of a liquid drop, a liquid wash, an ointment, a cream, a gel, a powder, a salve, a lotion, a foam, a spray, and a liposome.

3. The method of claim 2, wherein said bioactive formulation is administered topically to the ocular surface or the immediate vicinity of an eye of said subject.

4. The method of claim 2, wherein said administering comprises infusion of said bioactive formulation to an eye of said subject via a device selected from the group consisting of a pump-catheter system, a continuous or selective release device or material, and a contact lens.

5. The method of claim 2, wherein said administering is via a sustained release insert or implant, subconjunctival injection, intraocular injection, periocular injection, retrobulbar injection, or intracameral injection.

6. The method of claim 2, wherein said eye condition results at least in part from aqueous or evaporative dry eye disease, androgen deficiency, allergy, hyperosmolarity, keratoconjunctivitis sicca, meibomian gland disease, estrogen replacement therapy, refractive surgery, LASIK, corneal transplant, corneal ulcer, reduced tear film breakup time, compromised tear film, allergy, ocular surface disorders, increased protease levels in the tear film and at the ocular surface, chronic inflammation, Sjogren's syndrome, or a combination of any thereof.

7. The method of claim 2, comprising topically administering said bioactive formulation together with one or more ophthalmically acceptable agents selected from the group consisting of a demulcent, an excipient, an astringent, a vasoconstrictor, an emollient, and an electrolyte salt.

8. The method of claim 1, wherein said first cell line is a StemPro® human adipose-derived stem cell (ADSC) line provided by Life Technologies Catalog Number R7788115.

9. The method of claim 1, wherein said second cell line is a fetal human dermal fibroblast (HDF-f) cell line provided by ScienCell Research Laboratories Catalog Number 2300.

10. The method of claim 1, wherein said bioactive formulation further includes a third culture medium conditioned by cells of a third cell line.

11. The method of claim 10, wherein said third cell line is a limbal stem cell line.

12. The method of claim 1, wherein said first cell line is a StemPro® human adipose-derived stem cell (ADSC) line provided by Life Technologies Catalog Number R7788115, and said second cell line is a fetal human dermal fibroblast (HDF-f) cell line provided by ScienCell Research Laboratories Catalog Number 2300.

13. The method of claim 1, wherein each of said culturing steps is performed for at least 2 days, at least 5 days, at least 7 days, at least 8days, or at least 10 days.

14. The method of claim 1, wherein each of said culturing steps is carried out until said culture reaches at least 85%, at least 90%, at least 95%, or at least 98% cell confluence.

15. The method of claim 1, wherein cells of at least one of said cell lines have been passaged multiple times to produce said conditioned culture media.

16. The method of claim 15, wherein said cells have been passaged at least 2, 3, 4, 5, 6, 7, 8, 9, or 10 times to produce said conditioned culture media.

17. The method of claim 15, wherein cells of at least one of said cell lines are passaged after reaching at least 85%, at least 90%, at least 95%, or at least 98% cell confluence.

18. The method of claim 1, wherein said bioactive formulation comprises a ratio of said first conditioned culture medium to said second conditioned culture medium of between about 1:10 to about 10:1.

19. The method of claim 18, wherein said ratio is about 1:1.

20. The method of claim 1, wherein said culturing cells of said fetal fibroblast is carried out at 5% oxygen.

21. The method of claim 1, wherein said cells of said fetal fibroblast cell line have been passaged 10 times or fewer to produce said condition culture media.

* * * * *